US007910729B2

(12) United States Patent
Becker et al.

(10) Patent No.: US 7,910,729 B2
(45) Date of Patent: Mar. 22, 2011

(54) AZULENYL NITRONE SPIN TRAPPING AGENTS, METHODS OF MAKING AND USING SAME

(75) Inventors: David A. Becker, Parkland, FL (US); James J. Ley, Miami, FL (US)

(73) Assignee: The Florida International University Board of Trustees, Miami, FL (US)

( * ) Notice: Subject to any disclaimer, the term of this patent is extended or adjusted under 35 U.S.C. 154(b) by 770 days.

(21) Appl. No.: 11/662,352

(22) PCT Filed: Sep. 22, 2005

(86) PCT No.: PCT/US2005/034091
§ 371 (c)(1),
(2), (4) Date: Dec. 10, 2007

(87) PCT Pub. No.: WO2006/036768
PCT Pub. Date: Apr. 6, 2006

(65) Prior Publication Data
US 2008/0167474 A1 Jul. 10, 2008

Related U.S. Application Data

(60) Provisional application No. 60/612,143, filed on Sep. 22, 2004.

(51) Int. Cl.
*C07D 223/04* (2006.01)
(52) U.S. Cl. ...................................................... 540/604
(58) Field of Classification Search .................. 568/949;
540/604
See application file for complete search history.

(56) References Cited

U.S. PATENT DOCUMENTS

| | | | |
|---|---|---|---|
| 6,083,988 | A | 7/2000 | Becker |
| 6,197,825 | B1 | 3/2001 | Becker |
| 6,291,702 | B1 | 9/2001 | Becker |

FOREIGN PATENT DOCUMENTS

| | | |
|---|---|---|
| WO | WO 97/19054 | 5/1997 |
| WO | WO 2006/036768 | 4/2006 |

OTHER PUBLICATIONS

Belayev et al., J. Neurosurgery, (2002), vol. 96(6), pp. 1077-1083.*
Becker et al., "Stilbazulenyl Nitrone (STAZN): A Nitronyl-substituted Hydrocarbon with the Potency of Classical Phenolic Chain-breaking Antioxidants," *J. Am. Chem. Soc.*, 124:4678-4684 (2002).
Blanchard, "A Study of the Mechanism of Cumene Autoxidation. Mechanism of the Interaction of t-Peroxy Radicals," *J. Am. Chem. Soc.*, 81:4548-4552 (1959).
Block et al., "Effects of Antioxidants on Ischemic Retinal Dysfunction," *Exp. Eye Res.*, 64:559-564 (1997).
Bolli et al., "Demonstration of Free Radical Generation in 'Stunned' Myocardium of Intact Dogs with the Use of the Spin Trap Alpha-phenyl N-tert-butyl Nitrone," *J. Clin. Invest.*, 82:476-485 (1988).

Brasch, "Work in Progress: Methods of Contrast Enhancement for NMR Imaging and Potential Applications. A Subject Review," *Radiology*, 147:781-788 (1983).
Butterfield et al., "A Peptide Displays $H_2O_2$-like Reactivity Towards Aqueous $Fe^{2+}$, Nitroxide Spin Probes, and Synaptosomal Membrane Proteins," *Life Sci.*, 58:217-228 (1996).
Carney et al., "Reversal of Age-related Increase in Brain Protein Oxidation, Decrease in Enzyme Activity, and Loss in Temporal and Spatial Memory by Chronic Adminstration of the Spin-trapping Compound N-tert-butyl-alpha-phenylnitrone," *Proc. Natl. Acad. Sci. USA*, 88:3633-3636 (1991).
Chen et al., "Oxidative DNA Damage and Senescence of Human Diploid Fibroblast Cells," *Proc. Natl. Acad. Sci. USA*, 92:4337-4341 (1995).
Ciancarelli et al., "Urinary Nitric Oxide Metabolites and Lipid Peroxidation By-products in Migraine," *Cephalalgia*, 23:39-42 (2003).
Connor et al., "Evidence That Free Radicals Are Involved in Graft Failure Following Orthotopic Liver Transplantation in the Rat—An Electron Paramagnetic Resonance Spin Trapping Study," *Transplantation*, 54:199-204 (1992).
Dakhale et al., "Oxidative Damage and Schizophrenia: The Potential Benefit by Atypical Antipsychotics," *Neuropsychobiol.*, 49:205-209 (2004).
De las Heras Castano et al., "Use of Antioxidants to Treat Pain in Chronic Pacreatitis," *Rev. Esp. Enferm. Dig.*, 92:375-385 (2000).
Desnuelle et al., "A Double-blind, Placebo-controlled Randomized Clinical Trial of α-Tocopherol (Vitamin E) in the Treatment of Amyotrophic Lateral Sclerosis," *Amyotrophic Lateral Scler. Other Motor Neuron Disorders*, 2:9-18 (2001).
Downs et al., "Reduction in Endotoxin-induced Organ Dysfunction and Cytokine Secretion by a Cyclic Nitrone Antioxidant," *Int. J. Immunopharmacol.*, 17:571-580 (1995).
Edamatsu et al., "The Spin-Trap N-tert-alpha-phenyl-butylnitrone Prolongs the Life Span of the Senescence Accelerated Mouse," *Biochem. Biophys. Res. Commun.*, 211:847-849 (1995).
Esterbauer et al., "The Role of Vitamin E and Carotenoids in Prventing Oxidation of Low Density Lipoproteins," *Ann. NY Acad. Sci.*, 570:254-267 (1989).
Floyd et al., "Free Radical Damage to Protein and DNA: Mechanisms Involved and Relevant Observations on Brain Undergoing Oxidative Stress," *Ann. Neurol.* 32 Suppl:S22-S27 (1992).

(Continued)

*Primary Examiner* — Taofiq A Solola
(74) *Attorney, Agent, or Firm* — Marshall, Gerstein & Borun LLP

(57) ABSTRACT

The present invention provides azulenyl nitrones, such as those having the following general formula: (I) compositions comprising the same and methods of their use for the treatment or prevention of oxidative, ischemic, ischemia/reperfusion-related and chemokine-mediated conditions.

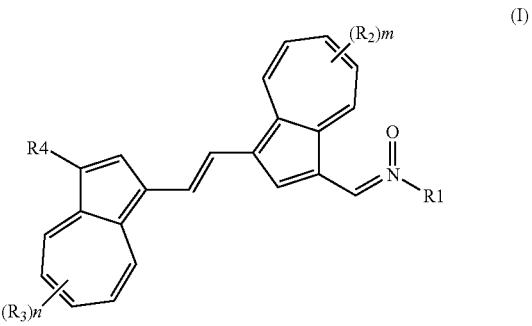

22 Claims, 1 Drawing Sheet

OTHER PUBLICATIONS

Floyd, "Oxidative Damage to Behavior During Aging," *Science*, 254:1597 (1991).

Fredriksson et al., MPTP-induced Deficits in Motor Activity: Neuroprotective Effectives of the Spin-trapping Agent, α-phenyl-tert-butylnitrone (PBN), *J. Neural. Transm.*, 104:579-592 (1997).

Freeman, "Shaped Radiofrequency Pulses in High Resolution NMR," *Prog. Nuc. Mag. Spec.*, 32:59-106 (1998).

Ginsberg et al., "Stilbazulenyl Nitrone, A Novel Antioxidant, Is Highly Neuroprotective in Focal Ischemia," *Ann. Neurol.* 54:330-342 (2003).

Gray et al., "Neuroprotective Effects of Nitrone Radical Scavenger S-PBN on Reperfusion Nerve Injury in Rats," *Brain Res.*, 982:179-185 (2003).

Gupta et al., "Add-on Melatonin Improves Quality of Life in Epileptic Children on Valproate Monotherapy: A Randomized, Double-blind, Placebo-controlled Trial," *Epilepsy Behav.*, 5:316-321 (2004).

Handelman et al., "Characterization of Products Formed During the Autoxidation of Beta-carotene," *Free Radic. Biol. Med.*, 10:427-437 (1991).

Harkins et al., "Effect of α-Phenyl-tert-butylnitrone on Endotoxin Toxemia in Horses," *Vet. Hum. Toxicol.*, 39:268-271 (1997).

Hensley et al., "Amyloid Beta-peptide Spin Trapping. 1: Peptide Enzyme Toxicity Is Related to Free Radical Spin Trap Reactivity," *Neuroreport.*, 6:489-492 (1995).

Kadkhodaee et al., "Detection of Hydroxyl and Carbon-centered Radicals by EPR Spectroscopy After Ischaemia and Reperfusion of the Rat Kidney," *Free Radical Res.*, 25:31-42 (1996).

Keana et al., "Influence of Structure on the Reduction of Nitroxide MRI Contrast-enhancing Agents by Ascorbate," *Physiol. Chem. Phys. Med. NMR*, 16:477-480 (1984).

Koiwai, "The Role of Oxygen Free Radicals in Experimental Acute Pancreatitis in the Rat," *Int. J. Pancreatol.*, 5:135-143 (1989).

Liu et al., "Bilirubin as a Potent Antioxidant Suppresses Experimental Autoimmune Encephalomyelitis: Implications for the Role of Oxidative Stress in the Development of Multiple Sclerosis," *J. Neuroimmunol.*, 139:27-35 (2003).

Marklund et al., "Effects of the Nitrone Radical Scavengers PBN and S-PBN on in vivo Trapping of Reactive Oxygen Species After Traumatic Brain Injury in Rats," *J. Cereb. Blood Flow Metab.*, 21:1259-1267 (2001).

Marshall et al., "NXY-059, A Free Radical-trapping Agent, Substantially Lessens the Functional Disability Resulting from Cerebral Ischemia in a Primate Species," *Stroke*, 32:190-198 (2001).

Micheletta et al., "Vitamin E Supplementation in Patients with Carotid Atherosclerosis: Reversal of Altered Oxidative Stress Status in Plasma But Not in Plaque," *Arterioscler. Thromb. Vasc. Biol.*, 24:136-140 (2004).

Murphy et al., "Direct Detection of Free Radical Generation in an in vivo Model of Acute Lung Injury," *Radical. Res. Commun.*, 15:167-176 (1991).

Nadeem et al., "Increased Oxidative Stress and Altered Levels of Antioxidants in Asthma," *J. Allergy Clin. Immunol.*, 111:72-78 (2003).

Nakao et al., "Antioxidant Treatment Protects Striatal Neurons Against Excitotoxic Insults," *Neuroscience*, 73:185-200 (1996).

Oliver et al., "Oxidative Damage to Brain Proteins, Loss of Glutamine Synthetase Activity, and Production of Free Radicals During Ischemia/Reperfusion-induced Injury to Gerbil Brain," *Proc. Natl. Acad. Sci. USA*, 87:5144-5147 (1990).

Ranjekar et al., "Decreased Antioxidant Enzymes and Membrane Essential Polyunsaturated Fatty Acids in Schizophrenic and Bipolar Mood Disorder Patients," *Psychiatry Res.*, 121:109-122 (2003).

Reimund et al., "Antioxidants Inhibit the in vitro Production of Inflammatory Cytokines in Crohn's Disease and Ulcerative Colitis," *Eur. J. Clin. Invest.*, 28:145-150 (1998).

Roza et al., "Free Radicals in Pancreatic and Cardiac Allograft Rejection," *Transplant. Proc.*, 26:544-545 (1994).

Sanders et al., "Spontaneous Oxygen Radical Production at Sites of Antigen Challenge in Allergic Subjects," *Am. J. Respir. Crit. Care Med.*, 151:1725-1733 (1995).

Sen et al., "α-Phenyl-tert-butylnitrone Inhibits Free Radical Release in Brain Concussion," *Free Radical Biol. Med.*, 16:685-691 (1994).

Socci et al., "Chronic Antioxidant Treatment Improves the Cognitive Performance of Aged Rats," *Brain Res.*, 693:88-94 (1995).

Steinberg et al., "Beyond Cholesterol. Modifications of Low-density Lipoprotein That Increase Its Atherogenicity," *N. Engl. J. Med.* 320:915-924 (1989).

Steinberg, "Clinical Trials of Antioxidants in Atherosclerosis: Are We Doing the Right Think?," *Lancet*, 346:36-38 (1995).

Strokov et al., "The Function of Endogenous Protective Systems in Patients with Insulin-Dependent Diabetes Mellitus and Polyneuropathy: Effect of Antioxidant Therapy," *Bull. Exp. Biol. Med.*, 130:986-990 (2000).

Tabatabaie et al., "Spin Trapping Agent Phenyl-N-tert-butylnitrone Protects Against the Onset of Drug-induced Insulin-dependent Diabetes Mellitus," *FEBS Lett.*, 407:148-152 (1997).

Vergely et al., "Effect of Two New PBN-derived Phosphorylated Nitrones Against Postischaemic Ventricular Dysrhythmias," *Fundam. Clin. Pharmacol.*, 17:433-442 (2003).

Vrca et al., "Supplementation with Antioxidants in the Treatment of Graves' Disease: The Effect on Glutathione Peroxidase Activity and Concentration of Selenium," *Clin. Chim. Acta*, 341:55-63 (2004).

Yamashita et al., "The Effects of α-Phenyl-tert-butylnitrone (PBN) on Copper-induced Rat Fulminant Hepatitis with Jaundice," *Free Radical Biol. Med.*, 21:755-761 (1996).

International Search Report for PCT/US2005/034091 dated Mar. 27, 2007.

Written Opinion for PCT/US2005/034091 dated Jul. 24, 2006.

* cited by examiner

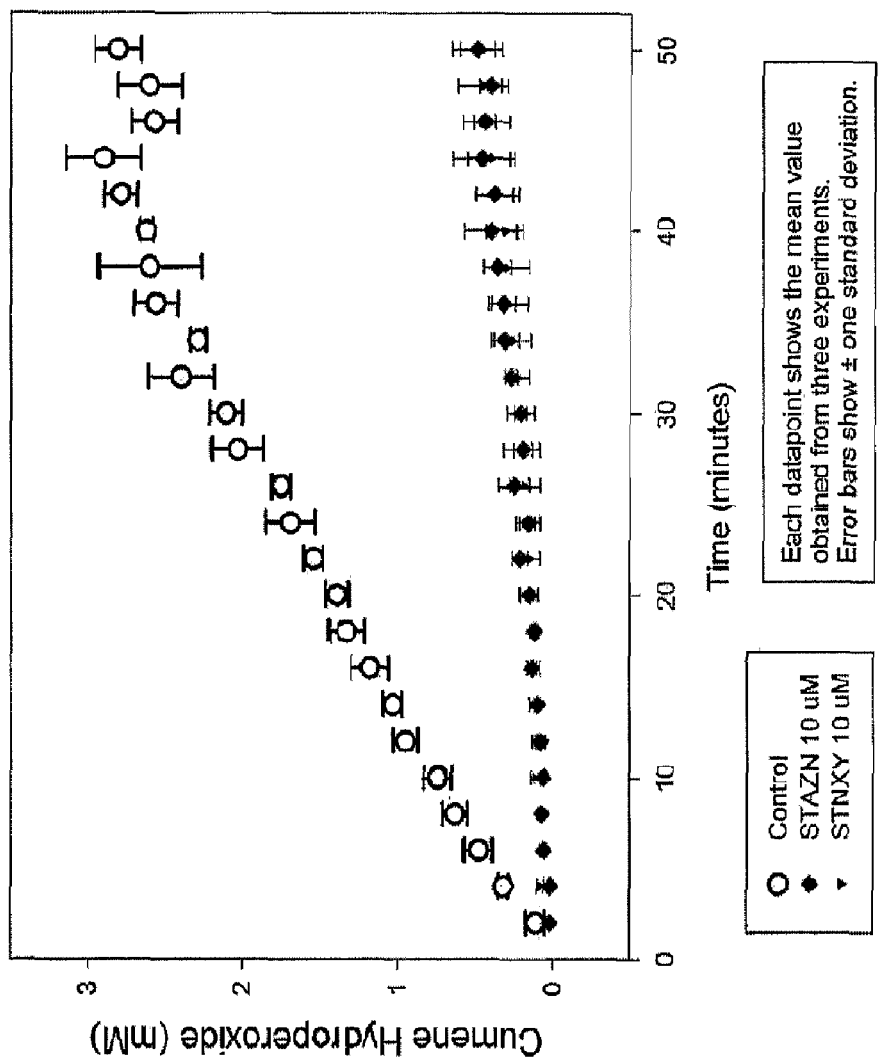
FIG. 1
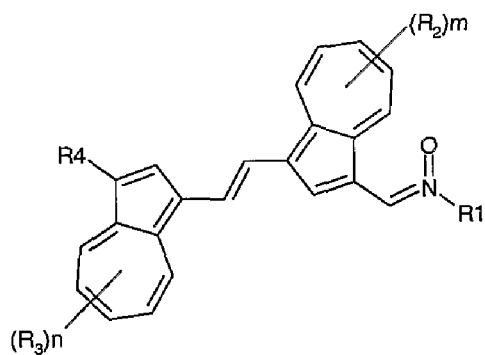

AZULENYL NITRONE SPIN TRAPPING AGENTS, METHODS OF MAKING AND USING SAME

CROSS-REFERENCE TO RELATED APPLICATIONS

This is the U.S. national phase application of International Application No. PCT/US2005/034091, filed Sep. 22, 2005, which claims the benefit of U.S. provisional application No. 60/612,143, filed Sep. 22, 2004.

FIELD OF THE INVENTION

The present invention relates to chromotropic azulenyl nitrone spin trapping agents, methods of making these agents, compositions comprising same, and methods of their use. In particular, azulenyl nitrones of the present invention are effective agents for trapping and identifying free radical species and find use as efficient antioxidants in physicochemical and biological systems.

BACKGROUND OF THE INVENTION

Nitrones behave as spin trapping agents when a diamagnetic nitrone compound (the "spin trap") reacts with a transient free radical species (having the "spin") to provide a relatively more stable radical species (referred to as the "spin adduct"). The spin adduct may be detectable by electron paramagnetic resonance (EPR) spectroscopy if the spin adduct has a reasonable lifetime. Thus, information about the spin can be gleaned from a study of the structure and spectroscopic characteristics of the spin adduct. For example, the toxicity of synthetic beta-amyloid peptide preparations toward glutamine synthetase could be correlated with the characteristics of the EPR signal generated by the spin adduct formed from each batch of synthetic beta-amyloid peptide and the spin trap PBN. See, Hensley, K. et al., in *NeuroReport* (1995) 6:489-492. Beta-amyloid peptides are neurotoxic substances that are postulated to be involved in the etiology of Alzheimer's disease.

Low molecular weight nitroxides are non-immunogenic. Moreover, they are typically cell permeable and can exist as a non-toxic, stable free radical capable of partitioning among various cellular compartments. Being paramagnetic, nitroxides are detectable by electron paramagnetic resonance (EPR) spectrometry and may serve as contrast agents in magnetic resonance imaging (MRI). See, Brasch, R. C, in *Radiology* (1983) 147:781; Keana, J. F. and Van, N. F., in *Physiol. Chem. Phys. Med. NMR* (1984) 16:477. Nitroxides have also been used as biophysical markers to probe cellular metabolism, oxygen level, intracellular pH, protein/lipid mobility and membrane structure. Hence, nitroxides find use in a number of diagnostic methods to determine the physiological/medical condition of a subject or the biophysical characteristics of a given sample, including samples obtained from a biological fluid.

Free radicals and oxidative damage have been implicated in brain aging and several neurodegenerative diseases. See, Socci, D. J. et al., in *Brain Research* (1995) 693(1-2):88-91. Chronic treatment of aged rats with certain compounds, including the spin, trapping agent alpha-phenyl N-tert-butylnitrone (PBN) and the antioxidant alpha-tocopherol (vitamin E), was found to benefit (i.e., improve) age-related changes in cognitive performance.

In vitro and in vivo evidence is mounting that the administration of antioxidants can strongly reduce the rate of progression of lesion formation associated with the process of atherosclerosis. Based on several experimental models, including low density lipoprotein (LDL)-receptor-deficient rabbits, cholesterol-fed rabbits and cholesterol-fed non-human primates, several antioxidants have manifested a 50-80% reduction in the rate of progression of lesions. The effectiveness of probucol, butylated hydroxytoluene (BHI), N,N'-diphenylphenylenediamine and vitamin E are attributed to their respective antioxidant potentials and to the proposition that oxidative modification of LDL contributes to the progression of atherosclerosis. See, Steinberg, D., in *Lancet* (1995) 346(8966):36-38. The one-electron oxidative potential (vs. NHE) of vitamin E in an aqueous solution at pH 7 and 20° C. is 0.48 V. The oxidative potentials of PBN, POBN and DMPO range from about 1.5-2.0 V.

Further, Downs, T. R. et al, in *Int'l J. Immunopharmacol.* (1995) 17(7):571-580, have shown that a cyclic nitrone antioxidant, MDL 101,002, reduces organ dysfunction, and cytokine secretion induced by lipopolysaccharide (LPS) administered to rats. These authors also tested the ability of MDL 101,002 to prevent LPS-induced pulmonary edema, leukopenia and thrombocytopenia. They found that MDL 101,002 prevented pulmonary edema, partially reduced thrombocytopenia but failed to prevent leukopenia. These workers found that their results were consistent with the role that oxygen free radicals played in the development of endotoxin-induced organ dysfunction and shock. They further suggest that free radical scavengers could reduce the mortality consequent to sepsis by organ dysfunction, at least in part, through a reduction in free radical-stimulated cytokine secretion.

Allergic reactions generate reactive oxygen species, including superoxide anions, which usher the influx of inflammatory cells to the site of allergen challenge and contribute to allergic inflammation. The inflammation may, in turn, lead to cell or tissue injury. For allergic reactions in the lung, these processes are also accompanied by increased vascular permeability and changes in airway mechanics. See, Sanders, S. P. et al. in *Am. J. Respir. Crit. Care Med.* (1995) 151:1725-1733. Thus, the administration of spin trapping agents to the site of challenge may reduce the inflammatory response and help reduce tissue or cell damage.

Separately, oxygen-derived free radicals are suspected in playing a role in cytotoxicity during episodes of allograft rejection/destruction following infiltration of the graft by mononuclear cells. The administration of radical scavengers may thus inhibit or reduce the incidence of allograft rejection. See, Roza, A. M. et al., in *Transplantation Proceedings* (1994) 26(2):544-545.

New reagents that could visually signal the formation of oxidative species would be extremely useful not only in skin tests or in cell culture but also in determining, for example, the compatibility of a patient's white blood cells with a particular kidney dialysis membrane. In vitro calorimetric assays would be of great utility.

PBN has been shown to offer protection in the cardiovascular disease area, in particular, by trapping free radicals generated during ischemia-reperfision-mediated injury to the heart. See, e.g., Bolli, R. et al. *J. Clin. Invest.* (1988) 82:476. The benefits of trapping free radicals generated in similar types of injury to the brain of experimental animals has also been demonstrated. See, e.g., Oliver, C. N. et al. *Proc. Nat'l. Acad. Sci. USA* (1990) 87:5144; Carney, J. M. et al. Ibid. (1991) 88:3636; Floyd, R. A. *Science* (1991) 254:1597. Oxidative damage to protein and DNA is mediated by oxygen free radical intermediates, leading to strand breaks and base modifications. Enzymes, such as glutamine synthetase, can also be inactivated by oxidative processes. Such damage can be observed, for example, in animals subjected to brain ischemia/reperfusion injury. See Floyd, R. A. and Carney, *J. M. Ann. Neurol*. (1992) 32:S22-S27.

Evidence is also available that PBN inhibits oxidative modification of cholesterol and triglycerides of Low Density Lipoproteins (LDL). Oxidative modification of LDL, along with lipid peroxidation and free-radical mediated reactions, is a process that is implicated in the initiation of atherosclerosis. See, e.g., Steinberg, D. et al., *N. Engl. J. Med*. (1989) 320:915; Esterbauer, H. et al. Ann. N.Y. Acad. Sci. (1989) 570:254.

Free radicals and oxidative damage have been proposed as the underlying reasons for aging, chronic and degenerative diseases of aging, and acute clinical conditions. Daily administration by intraperitoneal injection of PBN to an aged animal model showed that PBN offered a remarkable extension of the lifespan in both male and female populations. See, Packer, L. et al., in *Biochem. Biophys. Res. Commun*. (1995) 211(3):847-849. These authors conclude that PBN could have prophylatic value against the onset of, at least, pathological senescence.

Bruce N. Ames and co-workers, in an article published in the *Proc. Nat'l. Acad. Sci. USA* (1995) 92:4337-4341, found support for the hypothesis that oxidative DNA damage contributes to replicative cessation in human diploid fibroblast cells. These workers found that senescent cells, those cells that have ceased growth in culture after a finite number of population doublings, excise from DNA four times more 8-oxoguanine per day than do early-passage young cells. Also, levels of 8-oxo-2'-deoxyguanosine in DNA of senescent cells are about a third higher than those found in DNA of young cells. Most interestingly, they found that PBN, perhaps acting as either an antioxidant or as a spin trapping agent, effectively delayed the onset of senescence and rejuvenated near senescent cells.

International Application No. PCT/US96/18570, filed Nov. 15, 1996, discloses certain chromotropic nitrone spin trapping agents, methods for making these agents, and methods for their use. These compounds are effective in trapping free radicals, and thus have utility as antioxidants in biological systems. A series of U.S. Patents has issued based on this International Application, including U.S. Pat. Nos. 6,083,988; 6,197,825; and, 6,291,702.

Additional research with these and similar compounds was published on 3 Apr. 2002 in the Journal of the American Chemical Society: Becker et al., "Stilbazulenyl Nitrone (STAZN): A Nitronyl-Substituted Hydrocarbon with the Potency of Classical Phenolic Chain-Breaking Antioxidants", *J. Am. Chem. Soc*. 2002, 124:4678-84.

While the foregoing patents and related research presents, demonstrates and covers the structure and utility of a group of azulenyl nitrones, there exists a continuing need to discover additional new and effective substances exhibiting free radical/spin trapping and/or antioxidant activity which are potentially useful for a wide range of analytical, preservative, diagnostic, prophylactic and therapeutic applications. Accordingly, it is toward the satisfaction of such continuing need that the present invention is directed.

SUMMARY OF THE INVENTION

Accordingly, the present invention provides new and additional members of a class of azulenyl nitrone spin trapping agents, that, for example, can be efficiently prepared from abundant sesquiterpenes or their synthetic analogs. The azulenyl nitrones of the present invention expand upon the family of compounds described and covered in the above recited related patents, commonly assigned herewith, and further validate the therapeutic significance and value of this family. The activity of the compounds of the invention supports the utility of this family of azulenyl nitrones for alleviating a host of ill effects caused generally by reactive free radicals or oxidative processes in biological systems.

Therefore, it is an objective of the present invention to provide a compound of the general formula, below,

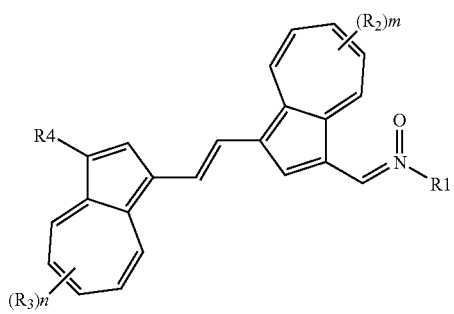

wherein
m and n is independently 0, 1, 2 or 3;
$R^1$ is selected from substituted or unsubstituted alkyl, cycloalkyl, heterocycloalkyl and aryl;
each of $R^2$ and $R^3$ is independently alkyl;
$R^4$ is H, substituted or unsubstituted alkyl, CHO, hydroxyl, substituted or unsubstituted alkoxy, substituted or unsubstituted alkoxycarbonyl, substituted or unsubstituted alkylthio, substituted or unsubstituted acylamino, substituted or unsubstituted amido, $SO_3H$, $C(H)=NOH$, $Cy^2$,

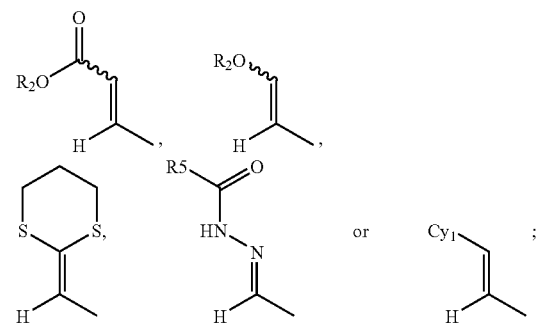

$R^5$ is amino, aminomethyl, dialkylaminomethyl, or trialkylaminomethyl quarternary salt; each of $Cy^1$ and $Cy^2$ is independently

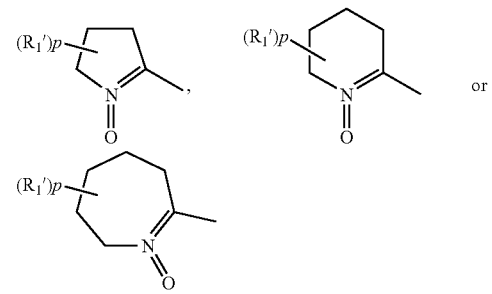

$R^{1'}$ is alkyl; p is 0, 1, or 2;
and
provided when $R^4$ is CHO, $R^1$ is selected from substituted alkyl, substituted aryl, substituted or unsubstituted cycloalkyl, and substituted or unsubstituted heterocycloalkyl;
or a pharmaceutically acceptable salt, solvate or prodrug thereof;
and stereoisomers and tautomers thereof.

In a second aspect, the present invention provides azulenyl nitrones according to formula II:

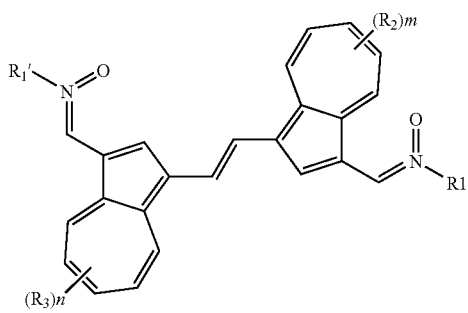

wherein
$R^1$ is selected from substituted alkyl, substituted aryl, substituted or unsubstituted cycloalkyl, and substituted or unsubstituted heterocycloalkyl;
$R^{1'}$ is selected from substituted or unsubstituted alkyl, cycloalkyl, heterocycloalkyl and aryl; each of $R^2$ and $R^3$ is independently alkyl;
or a pharmaceutically acceptable salt, solvate or prodrug thereof;
and stereoisomers and tautomers thereof.

In a third aspect, the present invention provides azulenyl nitrones according to formula III:

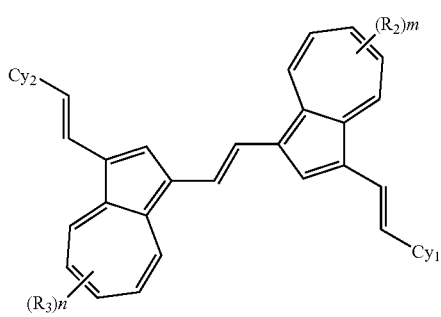

wherein
each of $R^2$ and $R^3$ is independently alkyl; and
each of $Cy^1$ and $Cy^2$ is independently

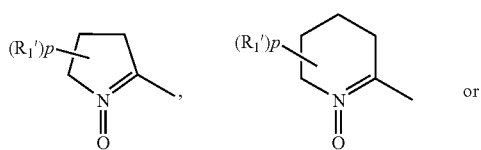

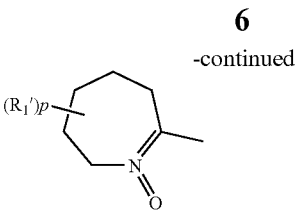

$R^{1'}$ is alkyl; p is 0, 1, or 2;
or a pharmaceutically acceptable salt, solvate or prodrug thereof; and stereoisomers and tautomers thereof.

In another aspect, the present invention provides pharmaceutical compositions comprising an azulenyl nitrone of the invention. The pharmaceutical compositions of the invention comprise an amount of the azulenyl nitrone effective to treat or prevent an oxidative, ischemic, ischemia/reperfusion-related or chemokine mediated condition in a subject. The compositions may be administered by a variety of routes, including, by example, orally and parenterally. In advantageous embodiments, the compounds are formulated for oral administration.

In a further aspect, the present invention provides unit dosage forms of an azulenyl nitrone of the invention for treating or preventing an oxidative, ischemic, ischemia/reperfusion-related or chemokine mediated condition in a subject. In certain embodiments the unit dosage forms comprise a pharmaceutical composition of an azulenyl nitrone in an amount effective to treat or prevent oxidative, ischemic, ischemia/reperfusion-related or chemokine mediated condition in a subject.

In a method of treatment or prophylaxis aspect, this invention provides a method of treating or prophylaxing a mammal susceptible to or afflicted with an oxidative, ischemic or ischemia/reperfusion-related condition. Exemplary conditions include, but are not limited to, neurological, cardiovascular and organ transplant-related conditions. The method comprises administering an effective amount of one or more of the azulenyl nitrones or pharmaceutical compositions described above. The compounds can be administered according to any technique known to those of skill in the art. In advantageous embodiments, the compounds are administered orally.

In a further method of treatment prohpylaxis aspect, the present invention provides a method of treating or prophylaxing a mammal susceptible to or afflicted with a condition modulated by a chemokine function or activity. Such conditions include, but are not limited to, neurodegenerative disease, peripheral neuropathies, infections, sequelae of infections and autoimmune diseases. The method comprises administering an effective amount of one or more of the azulenyl nitrones or pharmaceutical compositions described above.

In additional aspects, this invention provides methods for synthesizing the azulenyl nitrones of the invention.

BRIEF DESCRIPTION OF THE FIGURES

FIG. 1 is a graph of the results of antioxidant testing of compounds representative of the invention.

DETAILED DESCRIPTION OF THE INVENTION

The present invention provides the azulenyl nitrones, compositions comprising the azulenyl nitrones and methods of their use for treating or preventing oxidative, ischemic, ischemia/reperfusion-related or chemokine mediated disorders.

DEFINITIONS

When describing the azulenyl nitrones, pharmaceutical compositions and methods of this invention, the following terms have the following meanings unless otherwise specified.

"Acyl" refers to the group —C(O)R where R is hydrogen, alkyl, aryl or cycloalkyl.

"Acylamino" refers to the group —NRC(O)R where each R is independently hydrogen, alkyl, aryl or cycloalkyl.

"Acyloxy" refers to the group —OC(O)R where R is hydrogen, alkyl, aryl or cycloalkyl.

"Alkenyl" refers to a monovalent branched or unbranched unsaturated hydrocarbon group preferably having from 2 to 10 carbon atoms and more preferably 2 to 8 carbon atoms and having at least 1 and preferably from 1-2 sites of carbon-carbon double bond unsaturation. Preferred alkenyl groups include ethenyl (—CH=$CH_2$), n-propenyl (—$CH_2$CH=$CH_2$), isopropenyl (—C($CH_3$)=$CH_2$), and the like.

"Substituted alkenyl" refers to an alkenyl group having 1 or more substituents, for instance from 1 to 5 substituents, and preferably from 1 to 3 substituents, selected from the group consisting of acyl, acylamino, acyloxy, alkoxy, substituted alkoxy, alkoxycarbonyl, alkoxycarbonylamino, amino, substituted amino, aminocarbonyl, aminocarbonylamino, aminocarbonyloxy, aryl, aryloxy, azido, carboxyl, cyano, cycloalkyl, substituted cycloalkyl, halogen, hydroxyl, keto, nitro, thioalkoxy, substituted thioalkoxy, thioaryloxy, thioketo, thiol, alkyl-S(O)—, aryl-S(O)—, alkyl-S(O)$_2$— and aryl-S(O)$_2$—.

"Alkoxy" refers to the group —OR where R is alkyl. Preferred alkoxy groups include, by way of example, methoxy, ethoxy, n-propoxy, isopropoxy, n-butoxy, tert-butoxy, sec-butoxy, n-pentoxy, n-hexoxy, 1,2-dimethylbutoxy, and the like.

"Substituted alkoxy" refers to an alkoxy group having 1 or more substituents, for instance from 1 to 5 substituents, and preferably from 1 to 3 substituents, selected from the group consisting of acyl, acylamino, acyloxy, alkoxy, substituted alkoxy, alkoxycarbonyl, alkoxycarbonylamino, amino, substituted amino, aminocarbonyl, aminocarbonylamino, aminocarbonyloxy, aryl, aryloxy, azido, carboxyl, cyano, cycloalkyl, substituted cycloalkyl, halogen, hydroxyl, keto, nitro, thioalkoxy, substituted thioalkoxy, thioaryloxy, thioketo, thiol, alkyl-S(O)—, aryl-S(O)—, alkyl-S(O)$_2$— and aryl-S(O)$_2$—.

"Alkoxycarbonyl" refers to the group —C(O)OR where R is alkyl or cycloalkyl.

"Alkoxycarbonylamino" refers to the group —NRC(O)OR' where R is hydrogen, alkyl, aryl or cycloalkyl, and R' is alkyl or cycloalkyl.

"Alkyl" refers to a monovalent branched or unbranched saturated hydrocarbon group preferably having from 1 to about 11 carbon atoms, more preferably from 1 to 8 carbon atoms and still more preferably 1 to 6 carbon atoms. This term is exemplified by groups such as methyl, ethyl, n-propyl, isopropyl, n-butyl, isobutyl, tert-butyl, n-hexyl, n-octyl, tert-octyl and the like. The term "lower alkyl" refers to an alkyl group having from 1 to 11 carbon atoms.

"Substituted alkyl" refers to an alkyl group having 1 or more substituents, for instance from 1 to 5 substituents, and preferably from 1 to 3 substituents, selected from the group consisting of acyl, acylamino, acyloxy, alkoxy, substituted alkoxy, alkoxycarbonyl, alkoxycarbonylamino, amino, substituted amino, aminocarbonyl, aminocarbonylamino, aminocarbonyloxy, aryl, aryloxy, azido, carboxyl, cyano, cycloalkyl, substituted cycloalkyl, halogen, hydroxyl, keto, nitro, thioalkoxy, substituted thioalkoxy, thioaryloxy, thioketo, thiol, alkyl-S(O)—, aryl-S(O)—, alkyl-S(O)$_2$— and aryl-S(O)$_2$—.

"Alkylene" refers to a divalent branched or unbranched saturated hydrocarbon group preferably having from 1 to 10 carbon atoms and more preferably from 1 to 6 carbon atoms. This term is exemplified by groups such as methylene (—$CH_2$—), ethylene (—$CH_2CH_2$—), the propylene isomers (e.g., $CH_2CH_2CH_2$— and —CH($CH_3$)$CH_2$—) and the like.

"Substituted alkylene" refers to an alkylene group having 1 or more substituents, for instance from 1 to 5 substituents, and preferably from 1 to 3 substituents, selected from the group consisting of acyl, acylamino, acyloxy, alkoxy, substituted alkoxy, alkoxycarbonyl, alkoxycarbonylamino, amino, substituted amino, aminocarbonyl, aminocarbonylamino, aminocarbonyloxy, aryl, aryloxy, azido, carboxyl, cyano, halogen, hydroxyl, keto, nitro, thioalkoxy, substituted thioalkoxy, thioaryloxy, thioketo, thiol, alkyl-S(O)—, aryl-S(O)—, alkyl-S(O)$_2$— and aryl-S(O)$_2$—.

"Alkynyl" refers to a monovalent branched or unbranched unsaturated hydrocarbon group preferably having from 2 to 10 carbon atoms and more preferably 2 to 6 carbon atoms and having at least 1 and preferably from 1-2 sites of carbon-carbon triple bond unsaturation. Preferred alkynyl groups include ethynyl (—C≡CH), propargyl (—$CH_2$C≡CH) and the like.

"Substituted alkynyl" refers to an alkynyl group having 1 or more substituents, for instance from 1 to 5 substituents, and preferably from 1 to 3 substituents, selected from the group consisting of acyl, acylamino, acyloxy, alkoxy, substituted alkoxy, alkoxycarbonyl, alkoxycarbonylamino, amino, substituted amino, aminocarbonyl, aminocarbonylamino, aminocarbonyloxy, aryl, aryloxy, azido, carboxyl, cyano, cycloalkyl, substituted cycloalkyl, halogen, hydroxyl, keto, nitro, thioalkoxy, substituted thioalkoxy, thioaryloxy, thioketo, thiol, alkyl-S(O)—, aryl-S(O)—, alkyl-S(O)$_2$— and aryl-S(O)$_2$—.

"Amino" refers to the group —$NH_2$.

"Substituted amino" refers to the group —N(R)$_2$ where each R is independently selected from the group consisting of hydrogen, alkyl, substituted alkyl, alkenyl, substituted alkenyl, alkynyl, substituted alkynyl, aryl, cycloalkyl, substituted cycloalkyl, and where both R groups are joined to form an alkylene group. When both R groups are hydrogen, —N(R)$_2$ is an amino group.

"Alkylamino" refers to the group alkyl-NR'—, wherein R' is selected from hydrogen and alkyl.

"Arylamino" refers to the group aryl-NR'—, wherein R' is selected from hydrogen, aryl and heteroaryl.

"Alkoxyamino" refers to a radical —N(R)OR' where R is selected from hydrogen, alkyl and aryl; and R represents an alkyl or cycloalkyl group as defined herein.

"Alkylarylamino" refers to a radical —NRR' where R represents an alkyl or cycloalkyl group and R' is an aryl as defined herein.

"Aminocarbonyl" or "amido" refers to the group —C(O)NRR where each R is independently hydrogen, alkyl, aryl and cycloalkyl, or where the R groups are joined to form an alkylene group.

"Aminocarbonylamino" refers to the group —NRC(O)NRR where each R is independently hydrogen, alkyl, aryl or cycloalkyl, or where two R groups are joined to form an alkylene group.

"Aminocarbonyloxy" refers to the group —OC(O)NRR where each R is independently hydrogen, alkyl, aryl or cycloalkyl, or where the R groups are joined to form an alkylene group.

"Aryl" refers to an unsaturated aromatic carbocyclic group of from 6 to 14 carbon atoms having a single ring (e.g., phenyl) or multiple condensed rings (e.g., naphthyl or anthryl). Preferred aryls include phenyl, biphenyl, naphthyl and the like. Unless otherwise constrained by the definition for the individual substituent, such aryl groups can optionally be substituted with 1 or more substituents, for instance from 1 to 5 substituents, preferably 1 to 3 substituents, selected from the group consisting of acyl, acylamino, acyloxy, alkenyl, substituted alkenyl, alkoxy, substituted alkoxy, alkoxycarbonyl, alkyl, substituted alkyl, alkynyl, substituted alkynyl, amino, substituted amino, aminocarbonyl, aminocarbonylamino, aminocarbonyloxy, aryl, aryloxy, azido, carboxyl, cyano, cycloalkyl, substituted cycloalkyl, halogen, hydroxyl, nitro, thioalkoxy, substituted thioalkoxy, thioaryloxy, thiol, alkyl-S(O)—, aryl-S(O)—, alkyl-S(O)$_2$— and aryl-S(O)$_2$—.

"Aralkyl" or "arylalkyl" refers to an alkyl group, as defined above, substituted with one or more aryl groups, as defined above.

"Aryloxy" refers to the group —OR where R is aryl.

"Cycloalkyl" refers to a cyclic alkyl group of from 3 to 10 carbon atoms having a single cyclic ring or multiple condensed or bridged rings which can be optionally substituted with from 1 to 3 alkyl groups. Such cycloalkyl groups include, by way of example, single ring structures such as cyclopropyl, cyclobutyl, cyclopentyl, cyclooctyl, 1-methylcyclopropyl, 2-methylcyclopentyl, 2-methylcyclooctyl, and the like, or multiple or bridged ring structures such as adamantanyl and the like. The term "lower cycloalkyl" refers to a cycloalkyl group having from 3 to 6 carbon atoms.

"Substituted cycloalkyl" refers to a cycloalkyl group having 1 or more substituents, for instance from 1 to 5 substituents, and preferably from 1 to 3 substituents, selected from the group consisting of acyl, acylamino, acyloxy, alkoxy, substituted alkoxy, alkoxycarbonyl, alkoxycarbonylamino, amino, substituted amino, aminocarbonyl, aminocarbonylamino, aminocarbonyloxy, aryl, aryloxy, azido, carboxyl, cyano, cycloalkyl, substituted cycloalkyl, halogen, hydroxyl, keto, nitro, thioalkoxy, substituted thioalkoxy, thioaryloxy, thioketo, thiol, alkyl-S(O)—, aryl-S(O)—, alkyl-S(O)$_2$— and aryl-S(O)$_2$—.

"Cycloalkoxy" refers to the group —OR where R is cycloalkyl. Such cycloalkoxy groups include, by way of example, cyclopentoxy, cyclohexoxy and the like.

"Cycloalkenyl" refers to a cyclic alkenyl group of from 4 to 10 carbon atoms having a single cyclic ring and at least one point of internal unsaturation which can be optionally substituted with from 1 to 3 alkyl groups. Examples of suitable cycloalkenyl groups include, for instance, cyclopent-3-enyl, cyclohex-2-enyl, cyclooct-3-enyl and the like.

"Substituted cycloalkenyl" refers to a cycloalkenyl group having 1 or more substituents, for instance from 1 to 5 substituents, and preferably from 1 to 3 substituents, selected from the group consisting of acyl, acylamino, acyloxy, alkoxy, substituted alkoxy, alkoxycarbonyl, alkoxycarbonylamino, amino, substituted amino, aminocarbonyl, aminocarbonylamino, aminocarbonyloxy, aryl, aryloxy, azido, carboxyl, cyano, cycloalkyl, substituted cycloalkyl, halogen, hydroxyl, keto, nitro, thioalkoxy, substituted thioalkoxy, thioaryloxy, thioketo, thiol, alkyl-S(O)—, aryl-S(O)—, alkyl-S(O)$_2$— and aryl-S(O)$_2$—.

As used herein the term "cycloheteroalkyl" refers to a stable heterocyclic non-aromatic ring and fused rings containing one or more heteroatoms independently selected from N, O and S. A fused heterocyclic ring system may include carbocyclic rings and need only include one heterocyclic ring. Examples of heterocyclic rings include, but are not limited to, piperazinyl, homopiperazinyl, piperidinyl and morpholinyl, and are shown in the following illustrative examples:

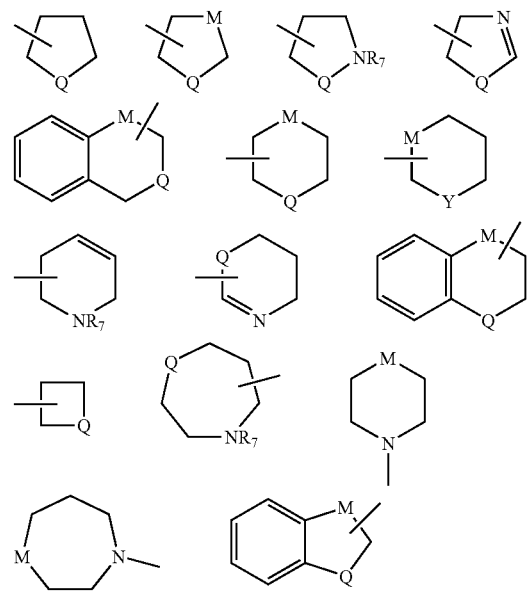

optionally substituted with one or more groups selected from the group consisting of acyl, acylamino, acyloxy, alkoxy, substituted alkoxy, alkoxycarbonyl, alkoxycarbonylamino, amino, substituted amino, aminocarbonyl, aminocarbonylamino, aminocarbonyloxy, aryl, aryloxy, azido, carboxyl, cyano, cycloalkyl, substituted cycloalkyl, halogen, hydroxyl, keto, nitro, thioalkoxy, substituted thioalkoxy, thioaryloxy, thioketo, thiol, alkyl-S(O)—, aryl-S(O)—, alkyl-S(O)$_2$— and aryl-S(O)$_2$—. Substituting groups include carbonyl or thiocarbonyl which provide, for example, lactam and urea derivatives. In the examples, M is $CR^7$, $NR_2$, O, or S; Q is O, $NR_2$ or S. $R^7$ and $R^8$ are independently selected from the group consisting of acyl, acylamino, acyloxy, alkoxy, substituted alkoxy, alkoxycarbonyl, alkoxycarbonylamino, amino, substituted amino, aminocarbonyl, aminocarbonylamino, aminocarbonyloxy, aryl, aryloxy, azido, carboxyl, cyano, cycloalkyl, substituted cycloalkyl, halogen, hydroxyl, keto, nitro, thioalkoxy, substituted thioalkoxy, thioaryloxy, thioketo, thiol, alkyl-S(O)—, aryl-S(O)—, alkyl-S(O)$_2$— and aryl-S(O)$_2$—.

As used herein, the term "heteroaryl" refers to an aryl ring system having one to four heteroatoms as ring atoms in a heteroaromatic ring system, wherein the remainder of the atoms are carbon atoms. Suitable heteroatoms include oxygen, sulfur and nitrogen. Preferably, the heterocyclic ring system is monocyclic or bicyclic. Nonlimiting examples include the following, which may be substituted with one or more $R^7$:

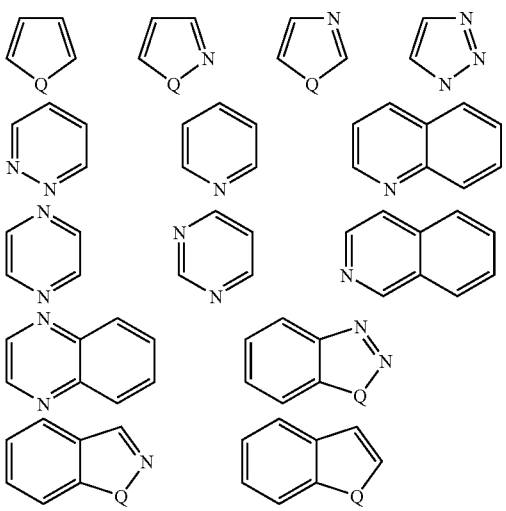

wherein $R^7$ and $R^8$ are each independently selected from hydrogen, lower alkyl, alkyl, alkenyl, alkynyl, cycloheteroalkyl, alkanoyl, alkoxy, aryloxy, heteroaryloxy, alkylamino, arylamino, heteroarylamino, $NR^{11}COR^{12}$, $NR^{11}SO_mR^{12}$ where m=1 or 2, COOalkyl, COOaryl, $CONR^{11}R^{12}$, $CONR^{11}R^{12}$, $NR^{11}R^{12}$, $SO_2NR^{11}R^{12}$, $S(O)_n$-alkyl or S(O)n-aryl where n is 0, 1 or 2; $R^7$ and $R^8$ may be joined to form a cyclic ring (saturated or unsaturated) from 5 to 8 atoms, optionally containing one or more heteroatoms selected from the group N, O or S; and $R^{11}$, $R^{12}$, and $R^{12}$ are independently hydrogen, alkyl, alkenyl, alkynyl, perfluoroalkyl, cycloalkyl, cycloheteroalkyl, aryl or heteroaryl.

"Halo" or "halogen" refers to fluoro, chloro, bromo and iodo. Preferred halo groups are either fluoro or chloro.

"Hydroxyl" refers to the group —OH.

"Keto" or "oxo" refers to the group =O.

"Nitro" refers to the group —$NO_2$.

"Thioalkoxy" or "alkylthio" refers to the group —SR where R is alkyl.

"Substituted thioalkoxy" refers to a thioalkoxy group having 1 or more substituents, for instance from 1 to 5 substituents, and preferably from 1 to 3 substituents, selected from the group consisting of acyl, acylamino, acyloxy, alkoxy, substituted alkoxy, alkoxycarbonyl, alkoxycarbonylamino, amino, substituted amino, aminocarbonyl, aminocarbonylamino, aminocarbonyloxy, aryl, aryloxy, azido, carboxyl, cyano, cycloalkyl, substituted cycloalkyl, halogen, hydroxyl, keto, nitro, thioalkoxy, substituted thioalkoxy, thioaryloxy, thioketo, thiol, alkyl-S(O)—, aryl-S(O)—, alkyl-S(O)$_2$— and aryl-S(O)$_2$—.

"Sulfanyl" refers to the radical HS—. "Substituted sulfanyl" refers to a radical such as RS— wherein R is any substituent described herein. In certain embodiments, "substituted sulfanyl" refers to a radical —SR where R is an alkyl or cycloalkyl group as defined herein that may be optionally substituted as defined herein. Representative examples include, but are not limited to, methylthio, ethylthio, propylthio, butylthio, and the like.

"Sulfinyl" refers to the radical —S(O)H. "Substituted sulfinyl" refers to a radical such as S(O)—R wherein R is any substituent described herein.

"Sulfonyl" refers to the divalent radical —S(O$_2$)—. "Substituted sulfonyl" refers to a radical such as —S(O$_2$)—R wherein R is any substituent described herein. "Aminosulfonyl" or "Sulfonamide" refers to the radical $H_2N(O_2)S$—, and "substituted aminosulfonyl" "substituted sulfonamide" refers to a radical such as $R_2N(O_2)S$— wherein each R is independently any substituent described herein. In certain embodiments, R is selected from H, lower alkyl, alkyl, aryl and heteroaryl.

"Thioaryloxy" refers to the group —SR where R is aryl.

"Thioketo" refers to the group =S.

"Thiol" refers to the group —SH.

The term "trialkylaminomethyl quarternary salt" refers to

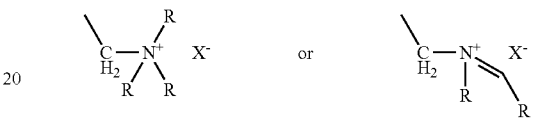

wherein R is alkyl or alkylene and X is halogen and wherein two R groups may join together to form a heterocyclic or heteroaryl ring. The nonlimiting examples of "trialkylaminomethyl quarternary salt" include the following

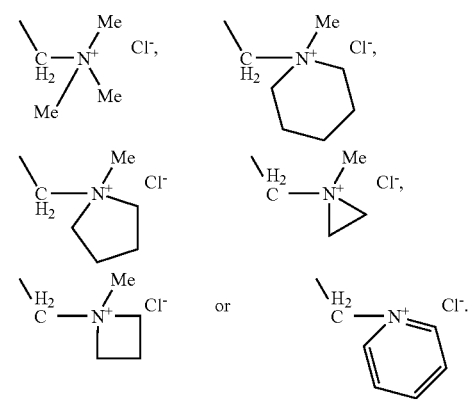

The term "subject" refers to an animal such as a mammal, including, but not limited to, primate (e.g., human), cow, sheep, goat, horse, dog, cat, rabbit, rat, mouse and the like. In preferred embodiments, the subject is a human.

The terms "treat," "treating" or "treatment," as used herein, refer to a method of alleviating or abrogating a disorder and/or its attendant symptoms. The terms "prevent," "preventing" or "prevention," as used herein, refer to a method of barring a subject from acquiring a disorder and/or its attendant symptoms. In certain embodiments, the terms "prevent," "preventing," or "prevention," refer to a method of reducing the risk of acquiring a disorder and/or its attendant symptoms.

"Pharmaceutically acceptable salt" refers to any salt of a compound of this invention which retains its biological properties and which is not biologically or otherwise undesirable. Such salts may be derived from a variety of organic and inorganic counter-ions well known in the art and include, by way of example illustration, sodium, potassium, calcium, magnesium, ammonium, tetraalkylammonium, and the like; and when the molecule contains a basic functionality, salts of organic or inorganic acids, such as hydrochloride, hydrobromide, tartrate, mesylate, acetate, maleate, oxalate and the like. The term "pharmaceutically-acceptable cation" refers to a pharmaceutically acceptable cationic counter-ion of an acidic functional group. Such cations are exemplified by sodium, potassium, calcium, magnesium, ammonium, tetraalkylammonium cations, and the like.

"Prodrugs" refers to compounds, including derivatives of the compounds of the invention, which have cleavable groups and become by solvolysis or under physiological conditions the compounds of the invention which are pharmaceutically active in vivo. Such examples include, but are not limited to, choline ester derivatives and the like, N-alkylmorpholine esters and the like.

"Solvate" refers to a compound of the present invention or a salt thereof, that further includes a stoichiometric or non-stoichiometric amount of solvent bound by non-covalent intermolecular forces. Where the solvent is water, the solvate is a hydrate.

The therapeutic methods and pharmaceutical compositions of the invention employ one or more azulenyl nitrones as the active agent. For the purposes of this invention, the nitrones of formula I are named using conventional nitrone nomenclature, i.e., the carbon atom of the carbon-nitrogen double bond (C=N) is designated the α-position and substituents on the nitrogen atom of the carbon-nitrogen double bond are given the N— prefix.

In some cases, the azulenyl nitrones of this invention may contain one or more chiral centers. Typically, such compounds will be prepared as a racemic mixture. If desired, however, such compounds can be prepared or isolated as pure stereoisomers, i.e., as individual enantiomers or diastereomers, or as stereoisomer-enriched mixtures. All such stereoisomers (and enriched mixtures) of the azulenyl nitrones of formula I are included within the scope of this invention. Pure stereoisomers (or enriched mixtures) may be prepared using, for example, optically active starting materials or stereoselective reagents well known in the art. Alternatively, racemic mixtures of such compounds can be separated using, for example, chiral column chromatography, chiral resolving agents and the like.

Additionally, all geometric isomers of the nitrone compounds of formula I are included within the scope of this invention including, for example, all isomers (i.e. E and Z isomers) of the carbon-nitrogen double bond of the nitrone functionality.

As used herein, the term "about" refers to a range of tolerance above or below a quantitative amount known to be acceptable to those of skill in the art. For instance, a dose of about 1000 mg indicates a dose typically administered under the guidance of a practitioner when a dose of 1000 mg is indicated. In certain embodiments, the term "about" refers to ±10% or ±5%.

Azulenyl Nitrones of the Invention

The present invention provides azulenyl nitrones useful for preventing and/or treating diseases and disorders related to oxidative conditions, ischemic conditions and ischemia/reperfusion-related or chemokine mediated conditions in mammals.

In certain embodiments, the present invention provides azulenyl nitrones according to formula (I):

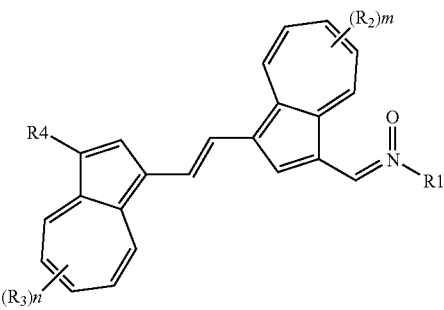

wherein
m and n is independently 0, 1, 2 or 3;
$R^1$ is selected from substituted or unsubstituted alkyl, cycloalkyl, heterocycloalkyl and aryl;
each of $R^2$ and $R^3$ is independently alkyl;
$R^4$ is H, substituted or unsubstituted alkyl CHO, hydroxyl, substituted or unsubstituted alkoxy, substituted or unsubstituted alkoxycarbonyl, substituted or unsubstituted alkylthio, substituted or unsubstituted acylamino, substituted or unsubstituted amido, $SO_3H$, $C(H)=NOH$, $Cy^2$,

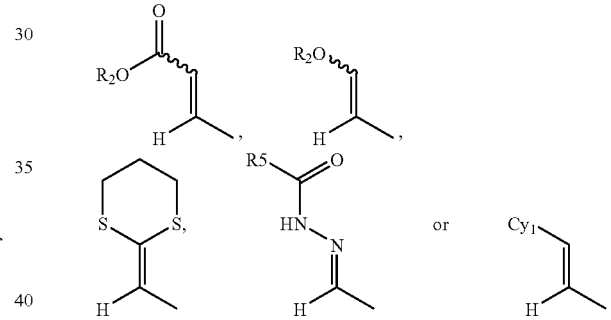

$R^5$ is amino, aminomethyl, dialkylaminomethyl, or trialkylaminomethyl quarternary salt;
each of $Cy^1$ and $Cy^2$ is independently

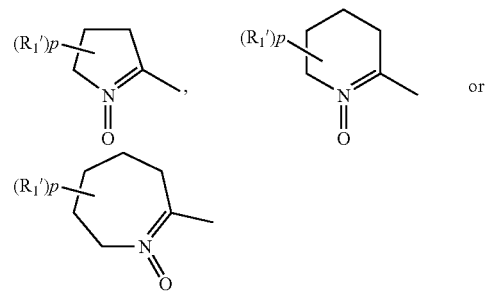

$R^{1'}$ is alkyl; p is 0, 1, or 2;
and provided when $R^4$ is CHO, $R^1$ is selected from substituted alkyl, substituted aryl, substituted or unsubstituted cycloalkyl, and substituted or unsubstituted heterocycloalkyl; or a pharmaceutically acceptable salt, solvate or prodrug thereof; and stereoisomers and tautomers thereof.

In formula (I) $R^1$ is selected from substituted or unsubstituted alkyl, cycloalkyl, heterocycloalkyl and aryl.

In one embodiment, for example, with respect to formula I, $R^1$ can be alkyl. In another embodiment $R^1$ is methyl, ethyl, propyl, butyl, t-butyl and the like. In certain embodiments, $R^1$ is t-butyl.

In one embodiment, for example, with respect to formula I, $R^1$ can be substituted alkyl. In another embodiment $R^1$ is substituted t-butyl. In further embodiments, $R^1$ is —C(CH$_2$CH$_2$CH$_2$OH)$_3$ or —C(Me)$_2$CH$_2$CH$_2$CO$_2$H. In certain embodiments, $R^1$ is —C(Me)$_2$CH$_2$CH$_2$CO$_2$Na.

In one embodiment, for example, with respect to formula I, $R^1$ can be substituted or unsubstituted cycloalkyl. In another embodiment $R^1$ is cyclopropyl, cyclobutyl, cyclopentyl, cyclohexyl or cycloheptyl. In certain embodiments, $R^1$ is cyclohexyl.

In one embodiment, for example, with respect to formula I, $R^1$ can be substituted or unsubstituted aryl. In another embodiment $R^1$ is substituted aryl. In certain embodiments, $R^1$ is substituted phenyl. In further embodiments, $R^1$ is phenyl substituted with SO$_3$H. In particular embodiments, $R^1$ is phenyl substituted with 3-SO$_3$H. In further particular embodiments, $R^1$ is phenyl substituted with 3-SO$_3$Na.

In one embodiment, for example, with respect to formula I, $R^2$ is selected from alkyl. In another embodiment $R^2$ is methyl. In a certain embodiment $R^2$ is iso-propyl.

In one embodiment, for example, with respect to formula I, m is selected from 0, 1, 2 and 3. In another embodiment, m is selected from 1 and 2. In a further embodiment m is 2.

In one particular embodiment, with respect to formula I, m is 2 and both $R^2$s are each methyl. In another embodiment, m is 2 and both $R^2$s are each isopropyl. In another embodiment, m is 2 and one of the $R^2$s is methyl and other is isopropyl.

In one embodiment, for example, with respect to formula I, $R^3$ is selected from alkyl.

In another embodiment $R^3$ is methyl. In a certain embodiment $R^3$ is iso-propyl.

In one embodiment, for example, with respect to formula I, n is selected from 0, 1, 2 and 3. In another embodiment, n is selected from 1 and 2. In a further embodiment n is 2.

In one particular embodiment, with respect to formula I, n is 2 and both $R^3$s are each methyl. In another embodiment, n is 2 and both $R^3$s are each isopropyl. In another embodiment, n is 2 and one of the $R^3$s is methyl and other is isopropyl.

In one embodiment, for example, with respect to formula I, $R^4$ is selected from H, alkyl, hydroxyl, alkoxy, CO$_2$alkyl, alkylthio, acylamino, amido, SO$_3$H, C(H)=NOH. In another embodiment $R^4$ is H.

In one embodiment, for example, with respect to formula I, $R^4$ is alkyl. In certain embodiments, $R^4$ is methyl.

In one embodiment, for example, with respect to formula I, $R^4$ is hydroxyl.

In one embodiment, for example, with respect to formula I, $R^4$ is alkoxy. In certain embodiments, $R^4$ is methoxy.

In one embodiment, for example, $R^4$ is alkylthio. In certain embodiments, $R^4$ is —SEt or —SMe.

In one embodiment, for example, with respect to formula I, $R^4$ is an ester group. In certain embodiments, $R^4$ is —CO$_2$alkyl. In further embodiments, $R^4$ is —CO$_2$Me or —CO2Et.

In one embodiment, for example, with respect to formula I, $R^4$ is an acylamino group. In certain embodiments, $R^4$ is —NHCOalkyl or —NMeCOalkyl. In further embodiments, $R^4$ is —NHCOMe.

In one embodiment, for example, with respect to formula I, $R^4$ is an amido group. In certain embodiments, $R^4$ is —CONH$_2$, —CONHalkyl or —CON(alkyl)$_2$. In further embodiments, $R^4$ is —CONH$_2$. In a further embodiment, $R^4$ is —CONHMe. In a further embodiment, $R^4$ is —CONMe$_2$. In a particular embodiment, $R^4$ is —CONH-t-butyl.

In one embodiment, for example, with respect to formula I, $R^4$ is a sulfonyl group. In certain embodiments, $R^4$ is —SO$_3$H. In further embodiments, $R^4$ is —SO$_3$Na.

In one embodiment, for example, with respect to formula I, $R^4$ is —C(H)=NOH.

In one embodiment, for example, with respect to formula I, $R^4$ is a Cy$^2$ group and Cy$^2$ is selected from

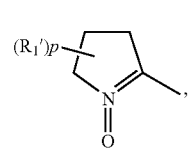 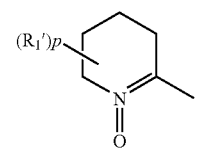 or

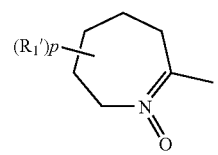

and $R^{1'}$ is alkyl; p is 0, 1, or 2.

In one embodiment with respect to formula I, $R^{1'}$ is alkyl. In a certain embodiment with respect to formula I, $R^{1'}$ is methyl.

In one embodiment, with respect to formula I, with respect to formula I, p is selected from 0, 1, and 2. In a certain embodiment p is 2.

In one embodiment, with respect to formula I, $R^4$ is

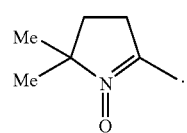

In another embodiment, with respect to formula I, $R^4$ is

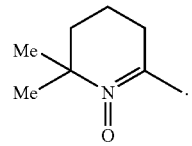

In another embodiment, with respect to formula I, $R^4$ is

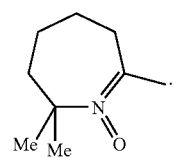

In one embodiment, with respect to formula I, $R^4$ is selected from

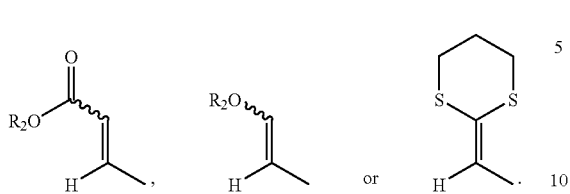

In one embodiment, with respect to formula I, $R^4$ is

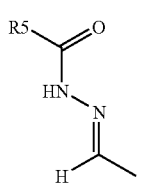

and $R^5$ is amino, aminomethyl, dialkylaminomethyl, or trialkylaminomethyl quarternary salt.

In one embodiment $R^5$ is —$CH_2NH_2$.
In one embodiment $R^5$ is —$CH_2NHMe$.
In one embodiment $R^5$ is —$CH_2NMe_2$.
In one embodiment $R^5$ is —$CH_2N{+}Me_3.Cl{-}$.
In one embodiment $R^5$ is —$CH_2N{+}Me_3.I{-}$.
In one embodiment $R^5$ is

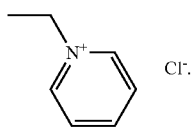

In one embodiment, with respect to formula I, $R^4$ is

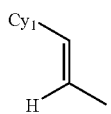

and $Cy^1$ is selected from

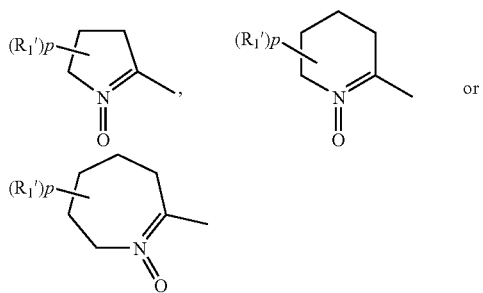

and $R^{1'}$ is alkyl; p is 0, 1, or 2.

In one embodiment, with respect to formula I, $R^{1'}$ is alkyl. In a certain embodiment $R^{1'}$ is methyl.

In one embodiment, with respect to formula I, p is selected from 0, 1, and 2. In certain embodiments p is 2.

In one embodiment, with respect to formula I, $Cy^1$ is

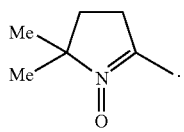

In another embodiment, with respect to formula I, $Cy^1$ is

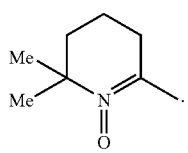

In another embodiment, with respect to formula I, $Cy^1$ is

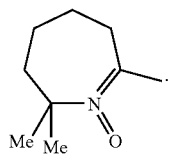

In a second aspect, the present invention provides azulenyl nitrones according to formula II:

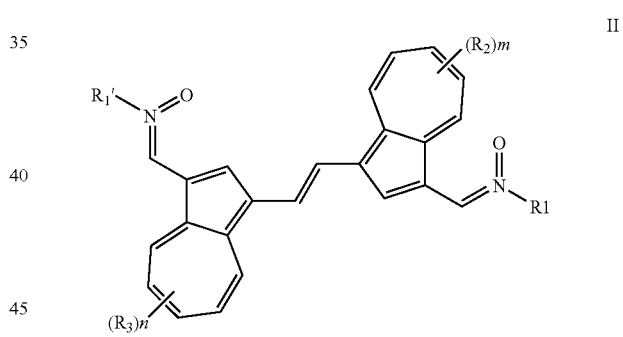

wherein
m and n is independently 0, 1, 2 or 3;
$R^1$ is selected from substituted alkyl, substituted aryl, substituted or unsubstituted cycloalkyl, and substituted or unsubstituted heterocycloalkyl;
$R^{1'}$ is selected from substituted or unsubstituted alkyl, cycloalkyl, heterocycloalkyl and aryl;
each of $R^2$ and $R^3$ is independently alkyl;
or a pharmaceutically acceptable salt, solvate or prodrug thereof; and stereoisomers and tautomers thereof.

In formula (II) $R^1$ is selected from substituted alkyl, substituted aryl, substituted or unsubstituted cycloalkyl, and substituted or unsubstituted heterocycloalkyl.

In one embodiment, for example, with respect to formula II, $R^1$ can be substituted alkyl. In another embodiment $R^1$ is substituted t-butyl. In certain embodiments, $R^1$ is —$C(CH_2CH_2CH_2OH)_3$ or —$C(Me)_2CH_2CH_2CO_2H$. In certain embodiments, $R^1$ is —$C(Me)_2CH_2CH_2CO_2Na$.

In one embodiment, for example, with respect to formula II, $R^1$ can be cycloalkyl. In another embodiment $R^1$ is cyclopropyl, cyclobutyl, cyclopentyl, cyclohexyl or cycloheptyl. In certain embodiments, $R^1$ is cyclohexyl.

In one embodiment, for example, with respect to formula II, $R^1$ can be substituted or unsubstituted aryl. In another embodiment $R^1$ is substituted aryl. In certain embodiments, $R^{1'}$ is substituted phenyl. In further embodiments, $R^1$ is phenyl substituted with $SO_3H$. In particular embodiments, $R^1$ is phenyl substituted with 3-$SO_3H$. In further particular embodiments, $R^1$ is phenyl substituted with 3-$SO_3Na$.

In formula (II) $R^1$ is selected from substituted or unsubstituted alkyl, cycloalkyl, heterocycloalkyl and aryl.

In one embodiment, for example, with respect to formula II, $R^{1'}$ can be alkyl. In another embodiment $R^{1'}$ is methyl, ethyl, propyl, butyl, t-butyl and the like. In certain embodiments, $R^{1'}$ is t-butyl.

In one embodiment, for example, with respect to formula II, $R^{1'}$ can be substituted alkyl. In another embodiment $R^{1'}$ is substituted t-butyl. In certain embodiments, $R^{1'}$ is —$C(CH_2CH_2CH_2OH)_3$ or —$C(Me)_2CH_2CH_2CO_2H$. In certain embodiments, $R^1$ is —$C(Me)_2CH_2CH_2CO_2Na$.

In one embodiment, for example, with respect to formula II, $R^{1'}$ can be substituted or unsubstituted cycloalkyl. In another embodiment $R^{1'}$ is cyclopropyl, cyclobutyl, cyclopentyl, cyclohexyl or cycloheptyl. In certain embodiments, $R^{1'}$ is cyclohexyl.

In one embodiment, for example, with respect to formula II, $R^{1'}$ can be substituted or unsubstituted aryl. In another embodiment $R^{1'}$ is substituted aryl. In certain embodiments, $R^{1'}$ is substituted phenyl. In further embodiments, $R^{1'}$ is phenyl substituted with $SO_3H$. In a particular embodiment, $R^{1'}$ is phenyl substituted with 3-$SO_3H$. In further particular embodiments, $R^1$ is phenyl substituted with 3-$SO_3Na$.

In one embodiment, for example, with respect to formula II, $R^2$ is selected from alkyl.

In another embodiment $R^2$ is methyl. In a certain embodiment $R^2$ is iso-propyl.

In one embodiment, for example, with respect to formula II, m is selected from 0, 1, 2 and 3. In another embodiment, m is selected from 1 and 2. In a further embodiment m is 2.

In one particular embodiment, with respect to formula II, m is 2 and both $R^2$s are each methyl. In another embodiment, m is 2 and both $R^2$s are each isopropyl. In another embodiment, m is 2 and one of the $R^2$s is methyl and other is isopropyl.

In one embodiment, for example, with respect to formula II, $R^3$ is selected from alkyl.

In another embodiment $R^3$ is methyl. In a certain embodiment $R^3$ is isopropyl.

In one embodiment, for example, with respect to formula II, n is selected from 0, 1, 2 and 3. In another embodiment, n is selected from 1 and 2. In a further embodiment n is 2.

In one particular embodiment, with respect to formula II, n is 2 and both $R^3$s are each methyl. In another embodiment, n is 2 and both $R^3$s are each isopropyl. In another embodiment, n is 2 and one of the $R^3$s is methyl and other is isopropyl.

In a third aspect, the present invention provides azulenyl nitrones according to formula III:

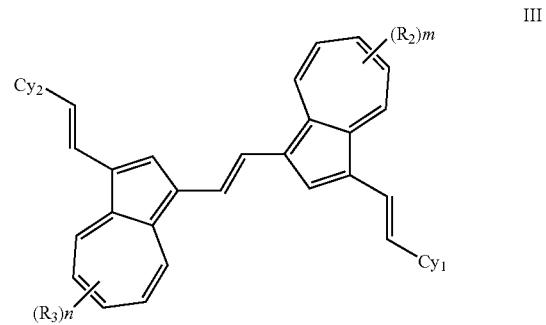

wherein
m and n is independently 0, 1, 2 or 3;
each of $R^2$ and $R^3$ is independently alkyl; and
each of $Cy^1$ and $Cy^2$ is independently

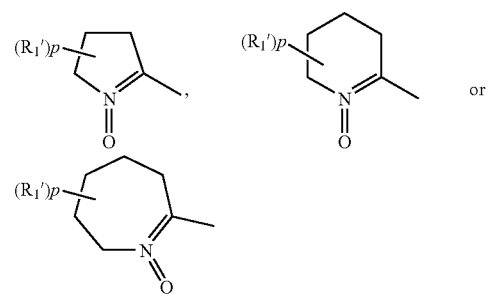

$R^{1'}$ is alkyl; p is 0, 1, or 2;
or a pharmaceutically acceptable salt, solvate or prodrug thereof;
and stereoisomers and tautomers thereof.

In one embodiment, for example, with respect to formula III, $R^2$ is selected from alkyl. In another embodiment $R^2$ is methyl. In a certain embodiment $R^2$ is isopropyl.

In one embodiment, for example, with respect to formula III, m is selected from 0, 1, 2 and 3. In another embodiment, m is selected from 1 and 2. In a further embodiment m is 2.

In one particular embodiment, with respect to formula III, m is 2 and both $R^2$s are each methyl. In another embodiment, m is 2 and both $R^2$s are each isopropyl. In another embodiment, m is 2 and one of the $R^2$s is methyl and other is isopropyl.

In one embodiment, for example, with respect to formula III, $R^3$ is selected from alkyl.

In another embodiment $R^3$ is methyl. In a certain embodiment $R^3$ is isopropyl.

In one embodiment, for example, with respect to formula III, n is selected from 0, 1, 2 and 3. In another embodiment, n is selected from 1 and 2. In a further embodiment n is 2.

In one particular embodiment, with respect to formula III, n is 2 and both $R^3$s are each methyl. In another embodiment, n is 2 and both $R^3$s are each isopropyl. In another embodiment, n is 2 and one of the $R^3$s is methyl and other is isopropyl.

In one embodiment, for example, with respect to formula III, $Cy^1$ is selected from

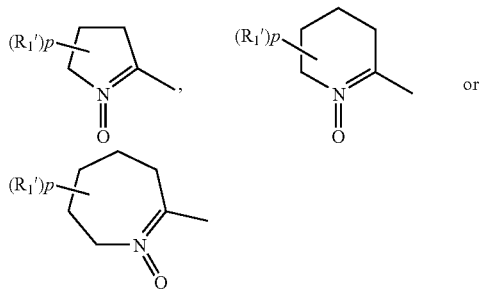

and $R^{1'}$ is alkyl; p is 0, 1, or 2.

In one embodiment, with respect to formula III, $R^{1'}$ is alkyl. In a certain embodiment $R^{1'}$ is methyl.

In one embodiment, with respect to formula III, p is selected from 0, 1, and 2. In a certain embodiment p is 2.

In one embodiment, with respect to formula III, $Cy^1$ is

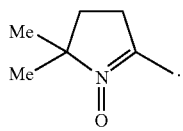

In another embodiment, with respect to formula III, $Cy^1$ is

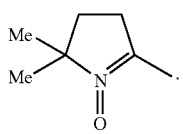

In another embodiment, with respect to formula III, $Cy^1$ is

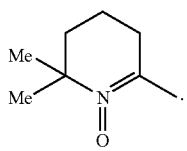

In one embodiment, for example, with respect to formula III, $Cy^2$ is selected from

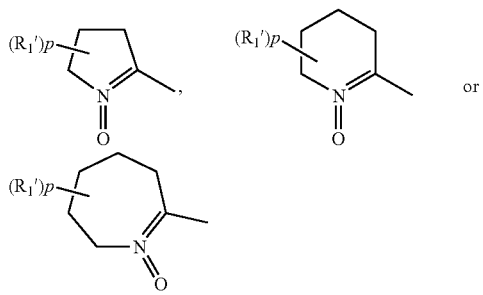

and $R^{1'}$ is alkyl; p is 0, 1, or 2.

In one embodiment, with respect to formula III, $R^{1'}$ is alkyl. In a certain embodiment $R^{1'}$ is methyl.

In one embodiment, with respect to formula III, p is selected from 0, 1, and 2. In certain embodiments p is 2.

In one embodiment, with respect to formula in, $Cy^2$ is

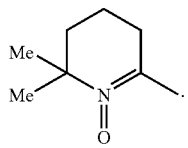

In another embodiment, with respect to formula III, $Cy^2$ is

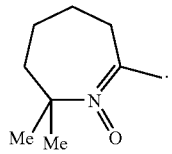

In another embodiment, with respect to formula III, $Cy^2$ is

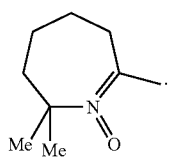

In a fourth aspect, the present invention provides azulenyl nitrones according to formula IIIa:

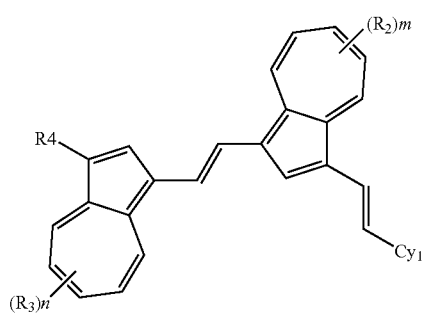

wherein m and n is independently 0, 1, 2 or 3;

each of $R^2$ and $R^3$ is independently alkyl;

$R^4$ is H, substituted or unsubstituted alkyl, CHO, hydroxyl, substituted or unsubstituted alkoxy, substituted or unsubstituted alkoxycarbonyl, substituted or unsubstituted alkylthio, substituted or unsubstituted acylamino, substituted or unsubstituted amido, $SO_3H$, $C(H)=NOH$, $Cy^2$,

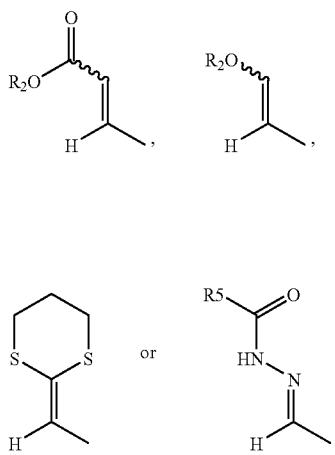

$R^5$ is amino, aminomethyl, dialkylaminomethyl, or trialkylaminomethyl quarternary salt; each of $Cy^1$ and $Cy^2$ is independently

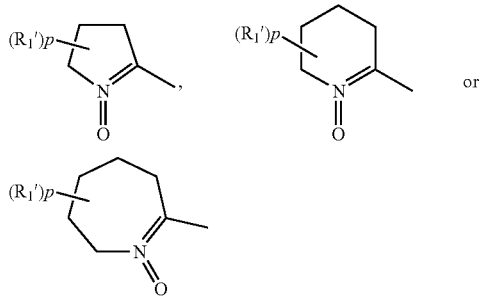

$R^{1'}$ is alkyl; p is 0, 1, or 2;

or a pharmaceutically acceptable salt, solvate or prodrug thereof; and stereoisomers and tautomers thereof.

In one embodiment, for example, with respect to formula IIIa, $R^2$ is selected from alkyl. In another embodiment $R^2$ is methyl. In a certain embodiment $R^2$ is isopropyl.

In one embodiment, for example, with respect to formula IIIa, m is selected from 0, 1, 2 and 3. In another embodiment, m is selected from 1 and 2. In a further embodiment m is 2.

In one particular embodiment, with respect to formula IIIa, m is 2 and both $R^2$s are each methyl. In another embodiment, m is 2 and both $R^2$s are each isopropyl. In another embodiment, m is 2 and one of the $R^2$s is methyl and other is isopropyl.

In one embodiment, for example, with respect to formula IIIa, $R^3$ is selected from alkyl. In another embodiment $R^3$ is methyl. In a certain embodiment $R^3$ is isopropyl.

In one embodiment, for example, with respect to formula IIIa, n is selected from 0, 1, 2 and 3. In another embodiment, n is selected from 1 and 2. In a further embodiment n is 2.

In one particular embodiment, with respect to formula IIIa, n is 2 and both $R^3$s are each methyl. In another embodiment, n is 2 and both $R^3$s are each isopropyl. In another embodiment, n is 2 and one of the $R^3$s is methyl and other is isopropyl.

In one embodiment, for example, with respect to formula IIIa, $Cy^1$ is selected from

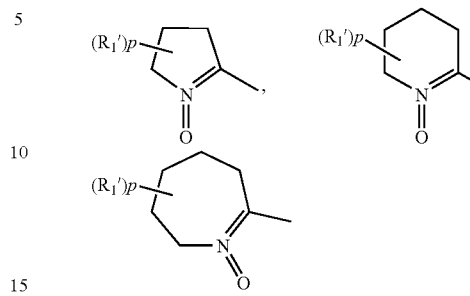

and $R^{1'}$ is alkyl; p is 0, 1, or 2.

In one embodiment, with respect to formula IIIa, $R^{1'}$ is alkyl. In a certain embodiment $R^{1'}$ is methyl.

In one embodiment, with respect to formula IIIa, p is selected from 0, 1, and 2. In a certain embodiment p is 2.

In one embodiment, with respect to formula IIIa, $Cy^1$ is

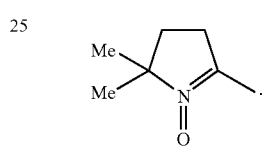

In another embodiment, with respect to formula IIIa, $Cy^1$ is

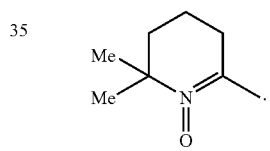

In another embodiment, with respect to formula IIIa, $Cy^1$ is

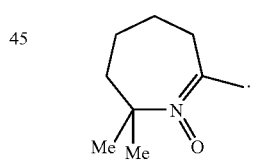

In one embodiment, for example, with respect to formula I, $R^4$ is selected from H, alkyl, hydroxyl, alkoxy, $CO_2$alkyl, alkylthio, acylamino, amido, $SO_3H$, C(H)=NOH. In another embodiment $R^4$ is H.

In one embodiment, for example, with respect to formula IIIa, $R^4$ is alkyl. In certain embodiments, $R^4$ is methyl.

In one embodiment, for example, with respect to formula IIIa, $R^4$ is hydroxyl.

In one embodiment, for example, with respect to formula IIIa, $R^4$ is alkoxy. In certain embodiments, $R^4$ is methoxy.

In one embodiment, for example, $R^4$ is alkylthio. In certain embodiments, $R^4$ is —SEt or —SMe.

In one embodiment, for example, with respect to formula IIIa, $R^4$ is an ester group. In certain embodiments, $R^4$ is —$CO_2$alkyl. In further embodiments, $R^4$ is —$CO_2$Me or —CO2Et.

In one embodiment, for example, with respect to formula IIIa, R⁴ is an acylamino group. In certain embodiments, R⁴ is —NHCOalkyl or —NMeCOalkyl. In further embodiments, R⁴ is —NHCOMe.

In one embodiment, for example, with respect to formula IIIa, R⁴ is an amido group. In certain embodiments, R⁴ is —CONH₂, —CONHalkyl or —CON(alkyl)₂. In further embodiments, R⁴ is —CONH₂. In a further embodiment, R⁴ is —CONHMe. In a further embodiment, R⁴ is —CONMe₂. In a particular embodiment, R⁴ is —CONH-t-butyl.

In one embodiment, for example, with respect to formula IIIa, R⁴ is a sulfonyl group. In certain embodiments, R⁴ is —SO₃H. In further embodiments, R⁴ is —SO₃Na.

In one embodiment, for example, with respect to formula IIIa, R⁴ is —C(H)=NOH.

In one embodiment, for example, with respect to formula IIIa, R⁴ is a Cy² group and Cy² is selected from

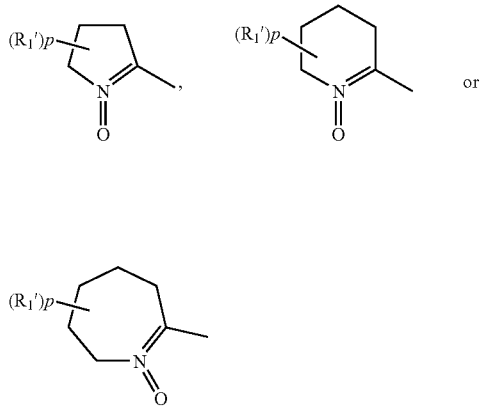

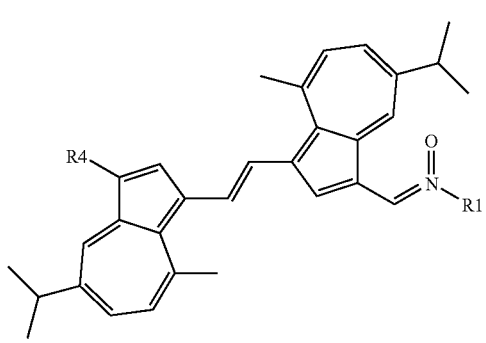

and $R^{1'}$ is alkyl; p is 0, 1, or 2.

In certain embodiments, the present invention provides azulenyl nitrones according to formula (IV):

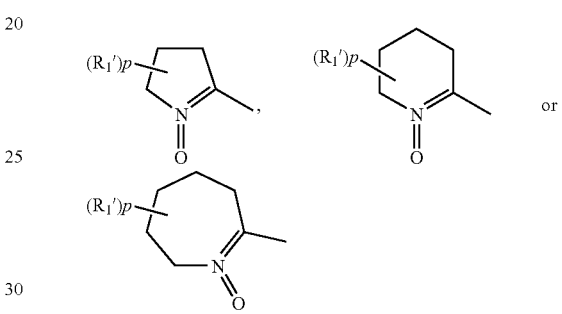

Wherein $R^1$ is selected from substituted or unsubstituted alkyl, cycloalkyl, heterocycloalkyl and aryl;

$R^4$ is H, substituted or unsubstituted alkyl, CHO, hydroxyl, substituted or unsubstituted alkoxy, substituted or unsubstituted alkoxycarbonyl, substituted or unsubstituted alkylthio, substituted or unsubstituted acylamino, substituted or unsubstituted amido, SO₃H, C(H)=NOH, Cy²,

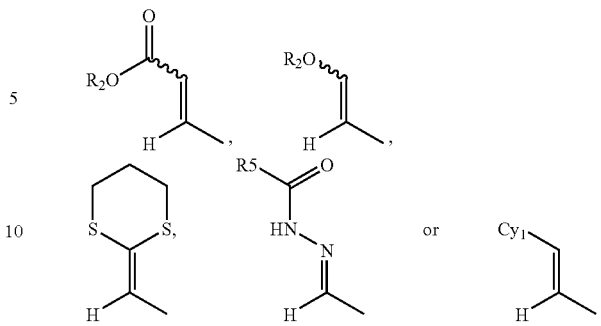

$R^5$ is amino, aminomethyl, dialkylaminomethyl, or trialkylaminomethyl quarternary salt; each of Cy¹ and Cy² is independently $R^{1'}$ is alkyl; p is 0, 1, or 2; and provided when R⁴ is CHO, R¹ is selected from substituted alkyl, substituted aryl, substituted or unsubstituted cycloalkyl, and substituted or unsubstituted heterocycloalkyl; or a pharmaceutically acceptable salt, solvate or prodrug thereof; and stereoisomers and tautomers thereof.

In formula (IV) R¹ is selected from substituted or unsubstituted alkyl, cycloalkyl, heterocycloalkyl and aryl.

In one embodiment, for example, with respect to formula IV, R¹ can be alkyl. In another embodiment R¹ is methyl, ethyl, propyl, butyl, t-butyl and the like. In certain embodiments, R¹ is t-butyl.

In one embodiment, for example, with respect to formula IV, R¹ can be substituted or unsubstituted alkyl. In another embodiment R¹ is substituted t-butyl. In certain embodiments, R¹ is —C(CH₂CH₂CH₂OH)₃ or —C(Me)₂CH₂CH₂CO₂H. In certain embodiments, R¹ is—C(Me)₂CH₂CH₂CO₂Na.

In one embodiment, for example, with respect to formula IV, R¹ can be cycloalkyl. In another embodiment R¹ is cyclopropyl, cyclobutyl, cyclopentyl, cyclohexyl or cycloheptyl. In certain embodiments, R¹ is cyclohexyl.

In one embodiment, for example, with respect to formula IV, R¹ can be substituted or unsubstituted aryl. In another embodiment R¹ is substituted aryl. In certain embodiments, R¹ is substituted phenyl. In further embodiments, R¹ is phenyl substituted with SO₃H. In a particular embodiment, R¹ is phenyl substituted with 3-SO₃H. In further particular embodiments, R¹ is phenyl substituted with 3-SO₃Na.

In one embodiment, for example, with respect to formula IV, R⁴ is selected from H, alkyl, hydroxyl, alkoxy, CO₂alkyl, alkylthio, acylamino, amido, SO₃H, C(H)=NOH. In another embodiment R⁴ is H.

In one embodiment, for example, with respect to formula IV, R⁴ is alkyl. In certain embodiments, R⁴ is methyl.

In one embodiment, for example, with respect to formula IV, $R^4$ is hydroxyl.

In one embodiment, for example, with respect to formula IV, $R^4$ is alkoxy. In certain embodiments, $R^4$ is methoxy.

In one embodiment, for example, $R^4$ is alkylthio. In certain embodiments, $R^4$ is —SEt or —SMe.

In one embodiment, for example, with respect to formula IV, $R^4$ is an ester group. In certain embodiments, $R^4$ is —$CO_2$alkyl. In further embodiments, $R^4$ is —$CO_2$Me or —$CO_2$Et.

In one embodiment, for example, with respect to formula IV, $R^4$ is an acylamino group. In certain embodiments, $R^4$ is —NHCOalkyl or —NMeCOalkyl. In further embodiments, $R^4$ is —NHCOMe.

In one embodiment, for example, with respect to formula IV, $R^4$ is an amido group. In certain embodiments, $R^4$ is —$CONH_2$, —CONHalkyl or —CON(alkyl)$_2$. In further embodiments, $R^4$ is —$CONH_2$. In further embodiment, $R^4$ is —CONHMe. In further embodiment, $R^4$ is —$CONMe_2$. In a particular embodiment, $R^4$ is —CONH-t-butyl.

In one embodiment, for example, with respect to formula IV, $R^4$ is a sulfonyl group. In certain embodiments, $R^4$ is —$SO_3H$. In further embodiments, $R^4$ is —$SO_3Na$.

In one embodiment, for example, with respect to formula IV, $R^4$ is —C(H)=NOH.

In one embodiment, for example, with respect to formula IV, $R^4$ is a $Cy^2$ group and $Cy^2$ is selected from

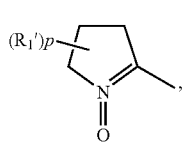 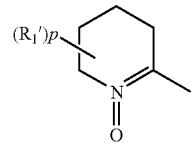 or

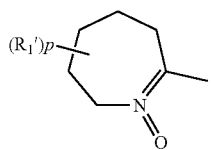

and $R^{1'}$ is alkyl; p is 0, 1, or 2.

In one embodiment, with respect to formula IV, $R^{1'}$ is alkyl. In a certain embodiment with respect to formula IV, $R^{1'}$ is methyl.

In one embodiment, with respect to formula IV, p is selected from 0, 1, and 2. In a certain embodiment with respect to formula IV, p is 2.

In one embodiment, with respect to formula IV, $R^4$ is

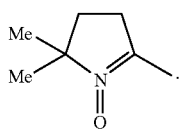

In another embodiment, with respect to formula IV, $R^4$ is

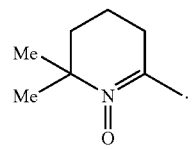

In another embodiment, with respect to formula IV, $R^4$ is

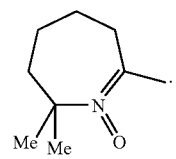

In one embodiment, with respect to formula IV, $R^4$ is selected from

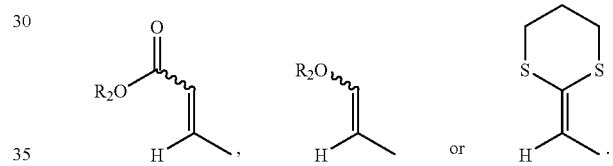

In one embodiment, with respect to formula IV, $R^4$ is

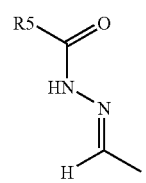

and $R^5$ is amino, aminomethyl, dialkylaminomethyl, or trialkylaminomethyl quarternary salt.

In one embodiment $R^5$ is —$CH_2NH_2$.

In one embodiment $R^5$ is —$CH_2NHMe$.

In one embodiment $R^5$ is —$CH_2NMe_2$.

In one embodiment $R^5$ is —$CH_2N+Me_3.Cl—$.

In one embodiment $R^5$ is —$CH_2N+Me_3.I—$.

In one embodiment $R^5$ is

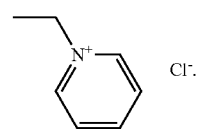

In one embodiment, with respect to formula IV, $R^4$ is

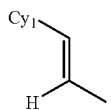

and $Cy^1$ is selected from

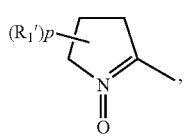 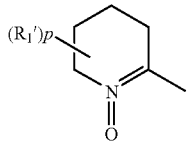 or

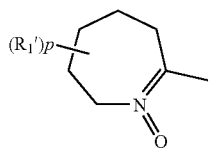

and $R^{1'}$ is alkyl; p is 0, 1, or 2.

In one embodiment, with respect to formula IV, $R^{1'}$ is alkyl. In a certain embodiment $R^{1'}$ is methyl.

In one embodiment, with respect to formula IV, p is selected from 0, 1, and 2. In a certain embodiment p is 2.

In one embodiment, with respect to formula IV, $Cy^1$ is

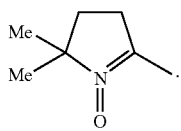

In another embodiment, with respect to formula IV, $Cy^1$ is

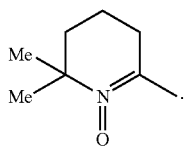

In another embodiment, with respect to formula IV, $Cy^1$ is

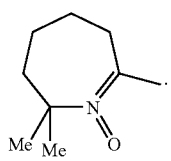

In an another aspect, the present invention provides azulenyl nitrones according to formula V:

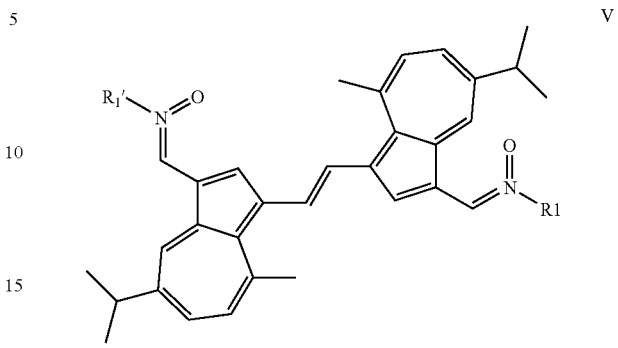

Wherein
$R^1$ is selected from substituted alkyl, substituted aryl, substituted or unsubstituted cycloalkyl, and substituted or unsubstituted heterocycloalkyl;
$R^1$ is selected from substituted or unsubstituted alkyl, cycloalkyl, heterocycloalkyl and aryl; or a pharmaceutically acceptable salt, solvate or prodrug thereof; and stereoisomers and tautomers thereof.

In formula (V) $R^1$ is selected from substituted alkyl, substituted aryl, substituted or unsubstituted cycloalkyl, and substituted or unsubstituted heterocycloalkyl.

In one embodiment, for example, with respect to formula V, $R^1$ can be substituted alkyl. In another embodiment $R^1$ is substituted t-butyl. In certain embodiments, $R^1$ is —$C(CH_2CH_2CH_2OH)_3$ or —$C(Me)_2CH_2CH_2CO_2H$. In certain embodiments, $R^1$ is —$C(Me)_2CH_2CH_2CO_2Na$.

In one embodiment, for example, with respect to formula V, $R^1$ can be cycloalkyl. In another embodiment $R^1$ is cyclopropyl, cyclobutyl, cyclopentyl, cyclohexyl or cycloheptyl. In certain embodiments, $R^1$ is cyclohexyl.

In one embodiment, for example, with respect to formula V, $R^1$ can be substituted or unsubstituted aryl. In another embodiment $R^1$ is substituted aryl. In certain embodiments, $R^1$ is substituted phenyl. In further embodiments, $R^1$ is phenyl substituted with $SO_3H$. In a particular embodiments, $R^1$ is phenyl substituted with 3-$SO_3H$.

In formula V, $R^{1'}$ is selected from substituted or unsubstituted alkyl, cycloalkyl, heterocycloalkyl and aryl.

In one embodiment, for example, with respect to formula V, $R^{1'}$ can be alkyl. In another embodiment $R^{1'}$ is methyl, ethyl, propyl, butyl, t-butyl and the like. In certain embodiments, $R^{1'}$ is t-butyl.

In one embodiment, for example, with respect to formula V, $R^{1'}$ can be substituted alkyl. In another embodiment $R^{1'}$ is substituted t-butyl. In certain embodiments, $R^{1'}$ is —$C(CH_2CH_2CH_2OH)_3$ or —$C(Me)_2CH_2CH_2CO_2H$. In certain embodiments, $R^1$ is —$C(Me)_2CH_2CH_2CO_2Na$.

In one embodiment, for example, with respect to formula V, $R^{1'}$ can be substituted or unsubstituted cycloalkyl. In another embodiment $R^{1'}$ is cyclopropyl, cyclobutyl, cyclopentyl, cyclohexyl or cycloheptyl. In certain embodiments, $R^{1'}$ is cyclohexyl.

In one embodiment, for example, with respect to formula V, $R^{1'}$ can be substituted or unsubstituted aryl. In another embodiment $R^{1'}$ is substituted aryl. In certain embodiments, $R^{1'}$ is substituted phenyl. In further embodiments, $R^{1'}$ is phenyl substituted with $SO_3H$. In a particular embodiment, $R^{1'}$ is phenyl substituted with 3-$SO_3H$.

In a third aspect, the present invention provides azulenyl nitrones according to formula VI:

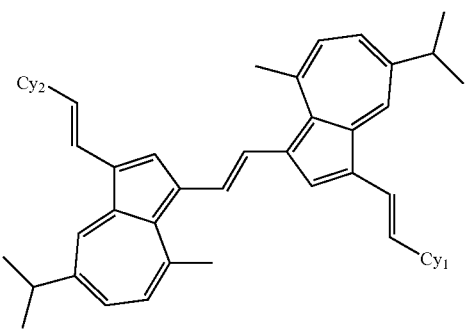

wherein
each of $Cy^1$ and $Cy^2$ is independently

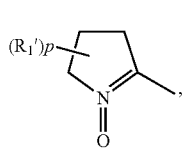 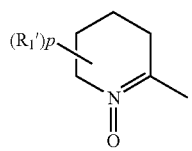 or

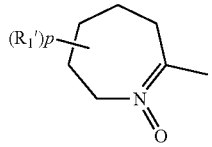

$R^{1'}$ is alkyl; p is 0, 1, or 2;
or a pharmaceutically acceptable salt, solvate or prodrug thereof; and stereoisomers and tautomers thereof.

In one embodiment, for example, with respect to formula VI, $Cy^1$ is selected from

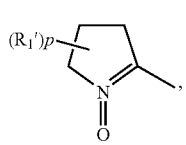 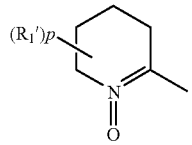 or

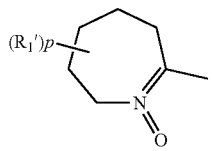

and $R^{1'}$ is alkyl; p is 0, 1, or 2.

In one embodiment, with respect to formula VI, $R^{1'}$ is alkyl. In a certain embodiment $R^{1'}$ is methyl.

In one embodiment, with respect to formula VI, p is selected from 0, 1, and 2. In certain embodiments p is 2.

In one embodiment, with respect to formula VI, $Cy^1$ is

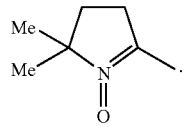

In another embodiment, with respect to formula VI, $Cy^1$ is

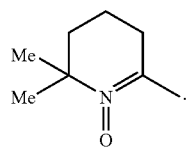

In another embodiment, with respect to formula VI, $Cy^1$ is

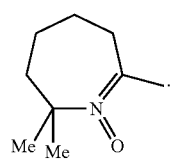

In one embodiment, for example, with respect to formula VI, $Cy^2$ is selected from

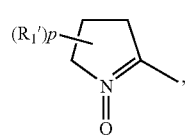 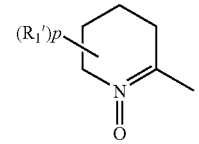 or

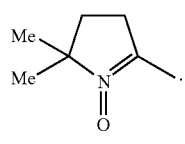

and $R^{1'}$ is alkyl; p is 0, 1, or 2.

In one embodiment, with respect to formula VI, $R^{1'}$ is alkyl. In a certain embodiment $R^{1'}$ is methyl.

In one embodiment, with respect to formula VI, p is selected from 0, 1, and 2. In certain embodiments p is 2.

In one embodiment, with respect to formula VI, $Cy^2$ is

In another embodiment, with respect to formula VI, Cy² is

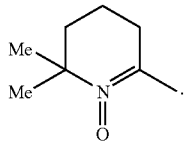

In another embodiment, with respect to formula VI, Cy² is

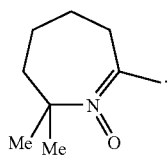

In an another aspect, the present invention provides azulenyl nitrones according to formula VII:

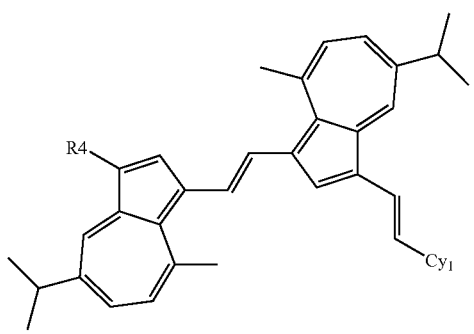

Wherein

R⁴ is H, substituted or unsubstituted alkyl, CHO, hydroxyl, substituted or unsubstituted alkoxy, substituted or unsubstituted alkoxycarbonyl, substituted or unsubstituted alkylthio, substituted or unsubstituted acylamino, substituted or unsubstituted amido, $SO_3H$, C(H)=NOH, Cy²,

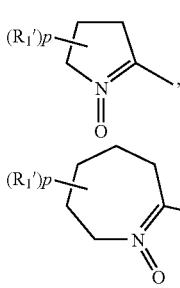

$R^5$ is amino, aminomethyl, dialkylaminomethyl, or trialkylaminomethyl quarternary salt; each of Cy¹ and Cy² is independently

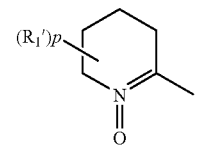

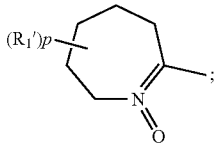

$R^{1'}$ is alkyl; p is 0, 1, or 2; and
or a pharmaceutically acceptable salt, solvate or prodrug thereof; and stereoisomers and tautomers thereof.

In one embodiment, for example, with respect to formula VII, Cy¹ is selected from

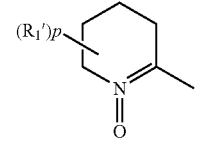

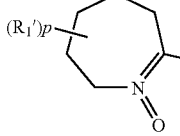

and $R^{1'}$ is alkyl; p is 0, 1, or 2.

In one embodiment, with respect to formula VII, $R^{1'}$ is alkyl. In a certain embodiment $R^{1'}$ is methyl.

In one embodiment, with respect to formula VII, p is selected from 0, 1, and 2. In a certain embodiment p is 2.

In one embodiment, with respect to formula VII, Cy¹ is

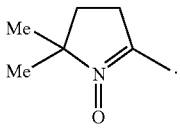

In another embodiment, with to formula VII, Cy¹ is

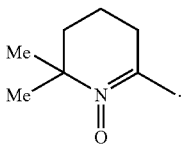

In another embodiment, with respect to formula VII, Cy¹ is

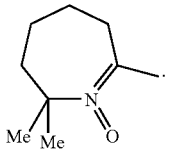

In one embodiment, for example, with respect to formula I, $R^4$ is selected from H, alkyl, hydroxyl, alkoxy, $CO_2$alkyl, alkylthio, acylamino, amido, $SO_3H$, $C(H)=NOH$. In another embodiment $R^4$ is H.

In one embodiment, for example, with respect to formula VII, $R^4$ is alkyl. In certain embodiments, $R^4$ is methyl.

In one embodiment, for example, with respect to formula VII, $R^4$ is hydroxyl.

In one embodiment, for example, with respect to formula VII, $R^4$ is alkoxy. In certain embodiments, $R^4$ is methoxy.

In one embodiment, for example, $R^4$ is alkylthio. In certain embodiments, $R^4$ is —SEt or —SMe.

In one embodiment, for example, with respect to formula VII, $R^4$ is an ester group. In certain embodiments, $R^4$ is —$CO_2$alkyl. In further embodiments, $R^4$ is —$CO_2$Me or —$CO_2$Et.

In one embodiment, for example, with respect to formula VII, $R^4$ is an acylamino group. In certain embodiments, $R^4$ is —NHCOalkyl or —NMeCOalkyl. In further embodiments, $R^4$ is —NHCOMe.

In one embodiment, for example, with respect to formula VII, $R^4$ is an amido group. In certain embodiments, $R^4$ is —$CONH_2$, —CONHalkyl or —CON(alkyl)$_2$. In further embodiments, $R^4$ is —$CONH_2$. In a further embodiment, $R^4$ is —CONHMe. In a further embodiment, $R^4$ is —$CONMe_2$. In a particular embodiment, $R^4$ is —CONH-t-butyl.

In one embodiment, for example, with respect to formula VII, $R^4$ is a sulfonyl group. In certain embodiments, $R^4$ is —$SO_3H$. In further embodiments, $R^4$ is —$SO_3Na$.

In one embodiment, for example, with respect to formula VII, $R^4$ is —$C(H)=NOH$.

In one embodiment, for example, with respect to formula VII, $R^4$ is a $Cy^2$ group and $Cy^2$ is selected from

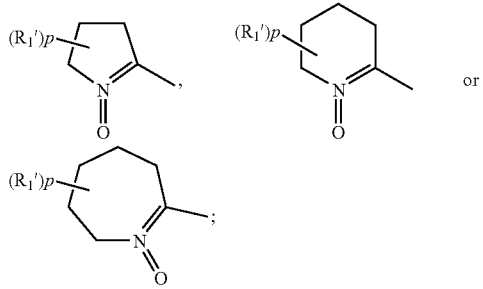

and $R^{1'}$ is alkyl; p is 0, 1, or 2.

Pharmaceutical Compositions

When employed as pharmaceuticals, the azulenyl nitrones of this invention are typically administered in the form of a pharmaceutical composition. Such compositions can be prepared in a manner well known in the pharmaceutical art and comprise at least one active compound. In preferred embodiments, the active compound is in purified form.

Generally, the compounds of this invention are administered in a pharmaceutically effective amount. The amount of the compound actually administered will typically be determined by a physician, in the light of the relevant circumstances, including the condition to be treated, the chosen route of administration, the actual compound administered, the age, weight, and response of the individual patient, the severity of the patient's symptoms, and the like.

The pharmaceutical compositions of this invention can be administered by a variety of routes including oral, rectal, transdermal, subcutaneous, intravenous, intramuscular, and intranasal. Depending on the intended route of delivery, the compounds of this invention are preferably formulated as either injectable or oral compositions or as salves, as lotions or as patches all for transdermal administration.

The compositions for oral administration can take the form of bulk liquid solutions or suspensions, or bulk powders. More commonly, however, the compositions are presented in unit dosage forms to facilitate accurate dosing. The term "unit dosage forms" refers to physically discrete units suitable as unitary dosages for human subjects and other mammals, each unit containing a predetermined quantity of active material calculated to produce the desired therapeutic effect, in association with a suitable pharmaceutical excipient. Typical unit dosage forms include prefilled, premeasured ampoules or syringes of the liquid compositions or pills, tablets, capsules or the like in the case of solid compositions. In such compositions, the active agent is usually a minor component (from about 0.1 to about 50% by weight or preferably from about 1 to about 40% by weight) with the remainder being various vehicles or carriers and processing aids helpful for forming the desired dosing form.

Liquid forms suitable for oral administration may include a suitable aqueous or nonaqueous vehicle with buffers, suspending and dispensing agents, colorants, flavors and the like. Solid forms may include, for example, any of the following ingredients, or compounds of a similar nature: a binder such as microcrystalline cellulose, gum tragacanth or gelatin; an excipient such as starch or lactose, a disintegrating agent such as alginic acid, Primogel, or corn starch; a lubricant such as magnesium stearate; a glidant such as colloidal silicon dioxide; a sweetening agent such as sucrose or saccharin; or a flavoring agent such as peppermint, methyl salicylate, or orange flavoring.

Injectable compositions are typically based upon injectable sterile saline or phosphate-buffered saline or other injectable carriers known in the art. As before, the active compound in such compositions is typically a minor component, often being from about 0.05 to 10% by weight with the remainder being the injectable carrier and the like.

Transdermal compositions are typically formulated as a topical ointment or cream containing the active ingredient(s), generally in an amount ranging from about 0.01 to about 20% by weight, preferably from about 0.1 to about 20% by weight, preferably from about 0.1 to about 10% by weight, and more preferably from about 0.5 to about 15% by weight. When formulated as a ointment, the active ingredients will typically be combined with either a paraffinic or a water-miscible ointment base. Alternatively, the active ingredients may be formulated in a cream with, for example an oil-in-water cream base. Such transdermal formulations are well-known in the art and generally include additional ingredients to enhance the dermal penetration of stability of the active ingredients or the formulation. All such known transdermal formulations and ingredients are included within the scope of this invention.

The compounds of this invention can also be administered by a transdermal device. Accordingly, transdermal administration can be accomplished using a patch either of the reservoir or porous membrane type or of a solid matrix variety.

The above-described components for orally administrable, injectable or topically administrable compositions are merely representative. Other materials as well as processing techniques and the like are set forth in Part 8 of *Remington's Pharmaceutical Sciences,* 17th edition, 1985, Mack Publishing Company, Easton, Pa., which is incorporated herein by reference.

The compounds of this invention can also be administered in sustained release forms or from sustained release drug delivery systems. A description of representative sustained release materials can be found in *Remington's Pharmaceutical Sciences*.

In another embodiment, the pharmaceutical compositions can be in unit dose or unit of use forms or packages. As is known to those of skill in the art, a unit dose form or package is a convenient, prescription size, patient ready unit labeled for direct distribution by health care providers. A unit of use form contains a pharmaceutical composition in an amount necessary for a typical treatment interval and duration for a given indication.

A unit dosage form contains a pharmaceutical composition in an amount necessary for administration of a single dose of the composition. The present invention provides unit dosage forms of pharmaceutical compositions in an amount for delivery of a dose of about 0.1 to 125 mg/kg of the azulenyl nitrone to a subject. The subject can be, for example, a human subject with an average weight of about 80 kg. In certain embodiments, the present invention provides a unit dosage form that comprises about 10, 25, 50, 100, 500, 1000, 2000 or 2500 mg of the azulenyl nitrone. In certain embodiments, the unit dosage form consists essentially of these amounts of the azulenyl nitrone; in other words, the unit dosage form can additionally comprise other ingredients for administration of the azulenyl nitrone such as pharmaceutically acceptable carrier, excipient or diluent, a vial, syringe, or patch or other ingredients known to those of skill in the art for administering the azulenyl nitrone.

Typical unit dosage forms include prefilled, premeasured ampoules or syringes of the injectable compositions or unit dose wrapped tablets or capsules in the case of solid, oral compositions. The unit dosage form can be, for example, a single use vial, a pre-filled syringe, a single transdermal patch and the like.

As is known to those of skill in the art, a unit of use form or package is a convenient, prescription size, patient ready unit labeled for direct distribution by health care providers. A unit of use form contains a pharmaceutical composition in an amount necessary for a typical treatment interval and duration for a given indication. The methods of the invention provide for a unit-of-use package of a pharmaceutical composition comprising, for example, an azulenyl nitrone in an amount sufficient to treat an average sized adult male or female with about 10, 25, 50, 100, 500, 1000, 2000 or 2500 mg orally or 10, 25, 50, 500, 1000, 2000 or 2500 mg subcutaneously three times weekly for one month. Thus a unit of use package as described above would have twelve (three times per week injections for four weeks) prefilled syringes each containing 10, 25, 50, 500, 1000, 2000 or 2500 mg of azulenyl nitrone pharmaceutical composition.

The pharmaceutical compositions can be labeled and have accompanying labeling to identify the composition contained therein and other information useful to health care providers and subjects in the treatment of the diseases and/or disorders described above, including, but not limited to, instructions for use, dose, dosing interval, duration, indication, contraindications, warnings, precautions, handling and storage instructions and the like.

The following formulation examples illustrate representative pharmaceutical compositions of this invention. The present invention, however, is not limited to the following pharmaceutical compositions.

Formulation 1

Tablets

A compound of the invention is admixed as a dry powder with a dry gelatin binder in an approximate 1:2 weight ratio. A minor amount of magnesium, stearate is added as a lubricant. The mixture is formed into 240-270 mg tablets (80-90 mg of active amide compound per tablet) in a tablet press.

Formulation 2

Capsules

A compound of the invention is admixed as a dry powder with a starch diluent in an approximate 1:1 weight ratio. The mixture is filled into 250 mg capsules (125 mg of active amide compound per capsule).

Formulation 3

Liquid

A compound of the invention (125 mg), sucrose (1.75 g) and xanthan gum (4 mg) are blended, passed through a No. 10 mesh U.S. sieve, and then mixed with a previously made solution of microcrystalline cellulose and sodium carboxymethyl cellulose (11:89, 50 mg) in water. Sodium benzoate (10 mg), flavor, and color are diluted with water and added with stirring. Sufficient water is then added to produce a total volume of 5 mL.

Formulation 4

Tablets

The compound of the invention is admixed as a dry powder with a dry gelatin binder in an approximate 1:2 weight ratio. A minor amount of magnesium stearate is added as a lubricant. The mixture is formed into 450-900 mg tablets (150-300 mg of active amide compound) in a tablet press.

Formulation 5

Injection

The compound of the invention is dissolved or suspended in a buffered sterile saline injectable aqueous medium to a concentration of approximately 5 mg/ml.

Formulation 6

Topical

Stearyl alcohol (250 g) and a white petrolatum (250 g) are melted at about 75° C. and then a mixture of a compound of the invention (50 g) methylparaben (0.25 g), propylparaben (0.15 g), sodium lauryl sulfate (10 g), and propylene glycol (120 g) dissolved in water (about 370 g) is added and the resulting mixture is stirred until it congeals.

Methods of Treatment and Prevention

The present azulenyl nitrones are used as therapeutic agents for the treatment of conditions in mammals. Accordingly, the compounds and pharmaceutical compositions of this invention find use as therapeutics for preventing and/or treating oxidative, ischemic, and ischemia/reperfusion-related and chemokine-mediated conditions in mammals including humans. Ischemia and ischemia/reperfusion-related conditions include neurological conditions and cardiovascular conditions as described below.

In a method of treatment or prophylaxis aspect, this invention provides a method of treating or prohpylaxing a mammal susceptible to or afflicted with a neurological condition such as stroke, multi-infarct dementia, traumatic brain injury, spinal cord injury, diabetic neuropathy or neurological sequelae of surgical procedures, which method comprises administering an effective amount of one or more of the pharmaceutical compositions just described. Neurological sequelae of surgical procedures include those sequelae of surgical procedures known to those of skill in the art such as neurological sequelae following procedures using a heart or a lung machine. In particular embodiments, the present invention provides methods of treating or preventing stroke with any compound of the invention.

In yet another method of treatment or prophylaxis aspect, this invention provides a method of treating or prophylaxing a mammal susceptible to or afflicted with a cardiovascular condition such as myocardial infarction, angina or a non-neurological organ or tissue injury following ischemia, which method comprises administering an effective amount of one or more of the pharmaceutical compositions just described. Non-neurological organ or tissue injury following ischemia include those conditions known to those of skill in the art to follow decreased blood flow or reperfusion following ischemia such as kidney ischemia, muscle ischemia, and the like.

In a further method of treatment or prophylaxis aspect, this invention provides a method of treating or prophylaxing a mammal susceptible to or afflicted with a condition related to chemokine function such as a neurodegenerative disease, a peripheral neuropathy, an infection, a sequela of an infection, or an autoimmune disease, which method comprises administering an effective amount of one or more of the pharmaceutical compositions just described.

Compounds that inhibit chemokine activity or function may be used for the treatment of diseases that are associated with inflammation, including but not limited to, inflammatory or allergic diseases such as asthma, allergic rhinitis, hypersensitivity lung diseases, hypersensitivity pneumonitis, eosinophilic pneumonias, delayed-type hypersensitivity, interstitial lung disease (ILD) (e.g., idiopathic pulmonary fibrosis, or ILD associated with rheumatoid arthritis, systemic lupus erythematosus, ankylosing spondylitis, systemic sclerosis, Sjögren's syndrome, polymyositis or dermatomyositis); systemic anaphylaxis or hypersensitivity responses, drug allergies, insect sting allergies; autoimmune diseases, such as rheumatoid arthritis, psoriatic arthritis, systemic lupus erythematosus, myastenia gravis, juvenile onset diabetes; glomerulonephritis, autoimmune throiditis, Alopecia Areata, Ankylosing Spondylitis, Antiphospholipid Syndrome, Autoimmune Addison's Disease, Autoimmune Hemolytic Anemia, Autoimmune Hepatitis, Behcet's Disease, Bullous Pemphigoid, Cardiomyopathy, Celiac Sprue-Dermatitis, Chronic Fatigue Immune Dysfunction Syndrome (CFIDS), Chronic Inflammatory Demyelinating Polyneuropathy, Cicatricial Pemphigoid, CREST Syndrome, Cold Agglutinin Disease, Crohn's Disease, Discoid Lupus, Essential Mixed Cryoglobulinemia, Fibromyalgia-Fibromyositis, Graves' Disease, Guillain-Barre, Hashimoto's Thyroiditis, Idiopathic Pulmonary Fibrosis, Idiopathic Thrombocytopenia Purpura, IgA Nephropathy, Insulin-dependent Diabetes, Juvenile Arthritis, Lichen Planus, Lupus, Ménière's Disease, Mixed Connective Tissue Disease, Multiple Sclerosis, Myasthenia Gravis, Pemphigus Vulgaris, Pernicious Anemia, Polyarteritis Nodosa, Polychondritis, Polyglandular Syndromes, Polymyalgia Rheumatica, Polymyositis and Dermatomyositis, Primary Agammaglobulinemia, Primary Biliary Cirrhosis, Psoriasis, Raynaud's Phenomenon, Reiter's Syndrome, Rheumatic Fever, Rheumatoid Arthritis, Sarcoidosis, Scleroderma, Sjögren's Syndrome, Stiff-Man Syndrome, Takayasu Arteritis, Temporal Arteritis/Giant Cell Arteritis, Ulcerative Colitis, Uveitis, Vasculitis, Vitiligo, Wegener's Granulomatosis, Churg-Strauss Syndrome, Atopic Allergy, Autoimmune Atrophic Gastritis, Achlorhydra Autoimmune, Cushings Syndrome, Dermatomyositis, Erythematosis, Goodpasture's Syndrome, Idiopathic Adrenal Atrophy, Lambert-Eaton Syndrome, Lupoid Hepatitis, Lymphopenia, Phacogenic Uveitis, Primary Sclerosing Cholangitis, Schmidt's Syndrome, Sympathetic Ophthalmia, Systemic Lupus Erythematosis, Thyrotoxicosis, Type B Insulin Resistance, Autoimmune ureitis, Autoimmune oophoritis and orchitis, Dermatitis herpetiformis.graft rejection, including allograft rejection or graft-versus-host disease; inflammatory bowel diseases, such as Crohn's disease and ulcerative colitis; spondyloarthropathies; scleroderma; psoriasis (including T-cell mediated psoriasis) and inflammatory dermatoses such as dermatitis, eczema, atopic dermatitis, allergic contact dermatitis, urticaria; vasculitis (e.g., necrotizing, cutaneous, and hypersensitivity vasculitis); eosinphilic myotis, eosiniphilic fasciitis; and cancers.

In addition compounds that activate or promote chemokine receptor function can be used for the treatment of diseases that are associated with immunosuppression such as individuals undergoing chemotherapy, radiation therapy, enhanced wound healing and burn treatment, therapy for autoimmune disease or other drug therapy (e.g., corticosteroid therapy) or combination of conventional drugs used in the treatment of autoimmune diseases and graft/transplantation rejection, which causes immunosuppression; immunosuppression due to congenital deficiency in receptor function or other causes; and infectious diseases, such as parasitic diseases, including but not limited to helminth infections, such as nematodes (round worms); Trichuriasis, Enterobiasis, Ascariasis, Hookworm, Strongyloidiasis, Trichinosis, filariasis; trematodes; visceral worms, visceral larva migtrans (e.g., Toxocara), eosinophilic gastroenteritis (e.g., *Anisaki* spp., *Phocanema* ssp.), cutaneous larva migrans (*Ancylostona braziliense, Ancylostoma caninum*); the malanra-causing protozoan *Plasmodium vivax, Human cytomegalovirus, Herpesvirus saimiri*, and Kaposi's sarcoma herpesvirus, also known as human herpesvirus 8, and poxvirus Moluscum contagiosum.

In certain embodiments, the present invention provides any compound of the invention for use in the manufacture of a medicament. In further embodiments, the present invention provides any compound of the invention for use in the manufacture of a medicament for the treatment or prevention of any condition identified herein. For instance, the present invention provides any compound of the invention for use in the manufacture of a medicament for the treatment and/or prevention of oxidative, ischemic, and ischemia/reperfusion-related and chemokine-mediated conditions in mammals including humans. Such conditions are described in detail herein.

Compounds of the present invention may be used in combination with any other active agents or pharmaceutical compositions where such combined therapy is useful to modulate chemokine receptor activity and thereby prevent and treat inflammatory and immunoregulatory diseases.

Injection dose levels range from about 0.1 mg/kg/hour to at least 15 mg/kg/hour, all for from about 1 to about 120 hours and especially 24 to 96 hours. A preloading bolus of from about 0.1 mg/kg to about 10 mg/kg or more may also be administered to achieve adequate steady state levels. The maximum total dose is not expected to exceed about 25 g/day for a 40 to 80 kg human patient. The present invention provides doses from about 0.1 mg to about 25 g per day for an 80 kg human patient. In particular embodiments, the present invention provides doses from about 0.1 mg to about 20 g per day, from about 0.1 mg to about 10 g per day, from about 0.1 mg to about 5 g per day, from about 0.1 mg to about 1 g per day, and from about 0.1 mg to about 0.5 g per day. Preferred doses for ischemic conditions include from about 0.1 mg to about 10 g per day, from about 50 mg to about 10 g per day, from about 100 mg to about 10 g per day, and from about 100 mg to about 1 g per day. Preferred doses for chemokine mediated disorders include from about 0.1 mg to about 10 g per day, from about 10 mg to about 1000 mg per day, and from about 100 mg to about 1000 mg per day.

For the prevention and/or treatment of long-term conditions, such as neurodegenerative and autoimmune conditions, the regimen for treatment usually stretches over many months or years so oral dosing is preferred for patient convenience and tolerance. With oral dosing, one to five and especially two to four and typically three oral doses per day are representative regimens. Using these dosing patterns, each dose provides from about 0.01 to about 65 mg/kg of the azulenyl nitrone, with preferred doses each providing from about 0.1 to about 20 mg/kg, about 0.1 to about 10 mg/kg and especially about 1 to about 5 mg/kg.

Transdermal doses are generally selected to provide similar or lower blood levels than are achieved using injection doses.

When used to prevent the onset of a neurodegenerative, autoimmune or inflammatory condition, the azulenyl nitrones of this invention will be administered to a patient at risk for developing the condition, typically on the advice and under the supervision of a physician, at the dosage levels described above. Patients at risk for developing a particular condition generally include those that have a family history of the condition, or those who have been identified by genetic testing or screening to be particularly susceptible to developing the condition.

The compounds of this invention can be administered as the sole active agent or they can be administered in combination with other agents, including other active azulenyl nitrones.

Methods of Making the Azulenyl Nitrones

The azulenyl nitrones of this invention can be prepared from readily available starting materials using the following general methods and procedures. It will be appreciated that where typical or preferred process conditions (i.e., reaction temperatures, times, mole ratios of reactants, solvents, pressures, etc.) are given, other proces conditions can also be used unless otherwise stated. Optimum reaction conditions may vary with the particular reactants or solvent used, but such conditions can be determined by one skilled in the art by routine optimization procedures.

Additionally, as will be apparent to those skilled in the art, conventional protecting groups may be necessary to prevent certain functional groups from undergoing undesired reactions. The choice of a suitable protecting group for a particular functional group as well as suitable conditions for protection and deprotection are well known in the art. For example, numerous protecting groups, and their introduction and removal, are described in T. W. Greene and P. G. M. Wuts, *Protecting Groups in Organic Synthesis*, Second Edition, Wiley, New York, 1991, and references cited therein.

Azulenyl nitrones of the invention can be prepared, for example, by reaction of an appropriately substituted carboxaldehyde derivative with an appropriately substituted hydroxylamine and the product isolated and purified by known standard procedures. Such procedures include, but are not limited to, recrystallization, column chromatography and HPLC.

The following synthetic and biological examples are offered to illustrate this invention and are not to be construed in any way as limiting the scope of this invention.

EXAMPLES

In the examples below, all temperatures are in degrees Celsius unless otherwise indicated. Examples 1-19 describe the synthesis of various azulenyl nitrones of this invention that have been or could be carried out. The graphical depictions of all the nitrone compounds illustrated herein are not intended to indicate the actual (E)- or (Z)-stereochemistry of the C=N double bond of the nitrone group. The present invention provides each stereoisomer of the compounds below.

NMR spectra were recorded employing either deuterated chloroform or DMSO as a solvent and using TMS as internal standard. Chemical shift values are quoted in parts per million (ppm) and coupling constants (J) in hertz (Hz).

Example 1

Synthesis of Mononitrone A

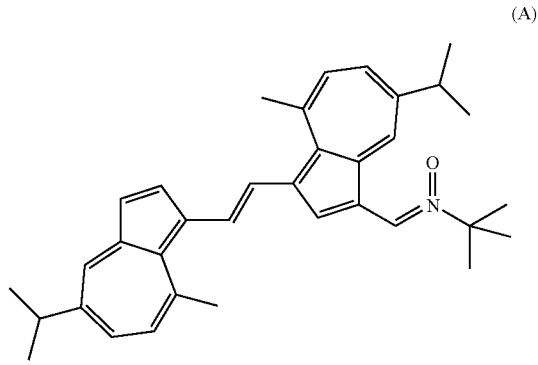

(A)

3-Trichloroacetylguaiazulene-1-carboxyaldehyde
(18)

Following a procedure similar of that of Kurokawa et al., guaiazulene (8.0 g, 41 mmol) was dissolved in 200 ml of dichloromethane. Trichloroacetic anhydride (51 g, 166 mmol, 4 equiv.) was added with stirring at room temperature. After 2 hours TLC showed no starting material. The solution was neutralized by the addition of a standard solution of sodium bicarbonate and vigorous shaking. The black/brown colored 3-trichloroacetylguaiazulene was extracted with dichloromethane and the solvent was removed under reduced pressure. The residue was dissolved in 450 ml of acetone and 50 ml of water was added to make a 9:1 acetone: water solution (v/v). Dichlordicynoquinone (DDQ) (27.9 g, 123 mmol, 3 equiv.) was added with stirring at room temperature. After half an hour TLC showed no starting material. Saturated sodium thiosulfate solution (200 ml) and saturated sodium bicarbonate solution (200 ml) were added to reduce and neutralize unreacted DDQ. Extraction of 18 with organic solvents is difficult because both phases are deeply colored and the propensity of the mixture is to form emulsions.

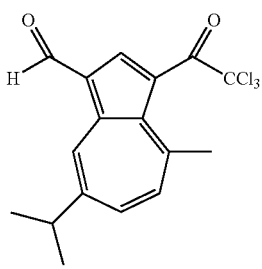

(18)

Extraction with hexane was achieved by adding hexane to the aqueous acetone mixture and decanting the upper phase into a separatory funnel, washing with water, and discarding the aqueous layer. The red colored organic phase was dried with magnesium sulfate and solvent was removed under reduced pressure until the solution was saturated. The saturated solution was loaded on to a silica gel column with hexane. A solution of 100:1 hexane:ethyl acetate (v/v) was used to elute 18, which after evaporation of the solvent, produced a red solid in 60% yield.

3-Bromoguaiazulene-1-carboxaldehyde (19)

A solution of aldehyde 18 (18.56 g, 52 mmol) in 1000 ml of acetone was stirred at 50° C. while 16.38 g (38 mmol, 1 equiv.) of Ba(OH)$_2$ in 200 ml of water was added. After 15 minutes the vessel was allowed to cool to room temperature. A layer of hexane was added and 13.88 g (78 mmol, 1.5 equiv.) of NBS was poured in. The flask was shaken vigorously. The hexane layer immediately became dark purple and the aldehyde 19 was isolated by exhaustive extraction with hexane.

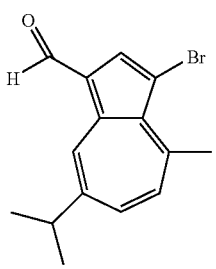

(19)

The volume of hexane was reduced until the solution became saturated. The product then was purified on a silica column. First the column was washed with hexane then the bromoaldehyde eluted with 50:1 hexane:ethyl acetate to yield 19 as a purple oil 14.27 g (94%). The aldehyde was rather unstable and was used immediately in the coupling reaction.

R$_f$ 0.52 EthOAc/Hexane (1:9); IR (KBr) 2959, 2927, 1647 (C=O), 1496, 1447, 1365, 1283, 1209, 1119 cm$^{-1}$; $^1$H NMR (400 MHz, CDCl$_3$) δ 1.39 (d, J=6.9 Hz, 6H), 3.16 (sept, J=6.9 Hz, H), 3.27 (s, 3H), 7.39 (d, J=10.8 Hz, 1H), 7.63 (dd, J=10.8, 2.1 Hz, H), 8.08 (s, 1H), 9.72 (d, J=2.1 Hz, H), 10.20 (s, H); $^{13}$C NMR (100 MHz, CDCl$_3$) δ 24.7, 28.0, 39.4, 102.6, 124.7, 134.0, 138.7, 138.8, 139.2, 140.0, 146.0, 150.1, 150.5, 186.1; LRMS (LC/MS APCI MeOH) m/e 291 (MH+[$^{79}$Br]), 293 (MH+[$^{81}$Br]); HRMS (FAB) calculated for C$_{15}$H$_{15}$BrO 290.03063 found 290.0310.

Trans-1,2-bis[3-(1-guaiazulenecarboxaldehyde)]ethylene (20)

The bromoaldehyde 19 (6.94 g, 23.8 mmol, 2.1 equiv.) and trans-bis(tri-n-butylstannyl)ethylene (6.858 g, 11.3 mmol, 1 equiv.) were dissolved in 50 mL of toluene. The flask was evacuated and filled with argon. Tetrakis(triphenylphosphonium)palladium (1.4 g, 5.8 mmol, 5 mol %) was added. The mixture was stirred under argon at 105° C. for 4 hours. The reaction mixture was chromatographed on a silica column. The column was first washed with hexane and the solvent polarity was slowly increased until the product was eluted with 10:1 hexane:ethyl acetate to afford 20, a black solid 4.08 g (81%) mp 232° C.; R$_f$ 0.15 EtOAc/Hexane (1:9); IR (KBr) 2956, 1643 (C=O), 1439, 1394, 1358, 1153, 945, 749 cm$^{-1}$; $^1$H NMR (400 MHz, CDCl$_3$) δ 1.43 (d, J=6.9 Hz, 12H), 3.17 (m, 8H), 7.34 (d, J=10.8 Hz, 2H), 7.56 (dd, J=10.8, 2.1 Hz, 2H), 7.62 (s, 2H), 8.4 (s, 2H), 9.655 (d, J=2.1 Hz, 2H), 10.35 (s, 2H); $^{13}$C NMR (100 MHz, CDCl$_3$) δ 24.8, 29.2, 38.5, 125.1, 126.5, 130.2, 133.3, 138.07, 138.13, 140.2, 142.0, 142.1, 149.9, 150.1, 186.9; LRMS (LC/MS APCI MeOH) m/e 449 (MH+); HRMS (FAB) calculated for C$_{32}$H$_{32}$O$_2$ 448.24023 found 448.2422.

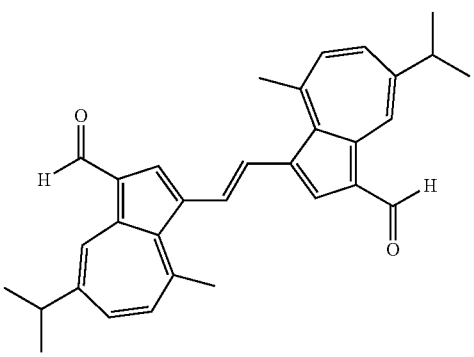

(20)

Trans-1-[3-(1-guaiazulenecarboxaldehyde)]-2-[3-(7-isopropyl-4-methylazulene)]ethylene (34)

Bisaldehyde 20 (100 mg, 0.22 mmol) was dissolved in 2 ml of toluene. Wilkinson's catalyst (209 mg, 0.22 mmol) was added and the mixture was stirred for 12 hours at 100° C. under argon. TLC showed least polar, green, di-decarbonylated product and brown mono-decarbonylated product 34 and a small amount of starting material. The product was isolated by silica gel column chromatography using chloroform as the eluting solvent. R$_f$ 0.3 Chloroform. IR (CHCl$_3$)

2957, 1642; ¹H NMR (400 MHz, CDCl₃) δ 1.38 (d, J=6.8 Hz, 6H), 1.44 (d, J=6.8 Hz, 6H, 3.04 (M, 1H), 3.15 (s, 3H), 3.18 (s, 3H), 3.2 (m, 1H), 6.98 (d, J=10.6 Hz, 1H), 7.56 (d, J=10.6, 1H), 7.68 (d, J=15.5 Hz, 1H), 7.89 (d, J=15.5 Hz, 1H), 8.10 (s, 1H), 8.17 (s, 1H), 8.43 (s, 1H); ¹³C NMR (100 MHz, D₂O) δ 24.7, 24.8, 29.02, 29.04, 37.9, 38.5, 119.8, 124.6, 125.2, 127.6, 128.3, 128.6, 129.4, 130.6, 131.2, 132.8, 133.0, 135.2, 135.9, 137.7, 137.9, 140.0, 142.0, 142.1, 142.7, 144.0, 147.4, 149.5, 150.2; LRMS (LC/MS APCI MeOH m/e 667 (MH+).

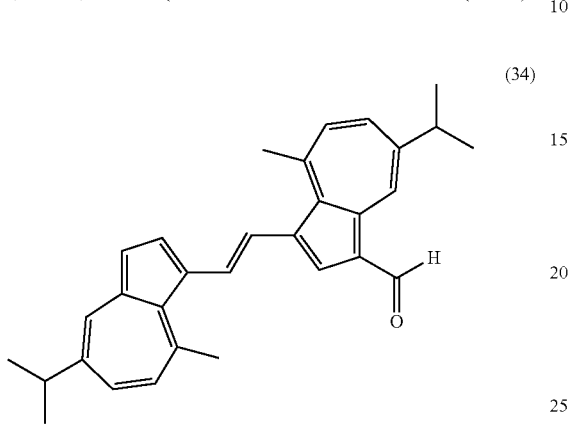

(34)

3-{(1E)-2-[8-Methyl-5-(methylethyl)azulenyl]vinyl}-4-methyl-7-(methylethyl)-1-vinylazulene Monoaldehyde 34 was converted to mononitrone A by reaction with N-tert-butylhydroxylamine hydrochloride in pyridine at 100° C. ¹H NMR (400 MHz, CDCl₃) δ 1.33 (d, J=6.8 Hz, 6H), 1.36 (d, J=6.8 Hz, 6H), 1.58 (s, 9H), 2.98 (m, 1H), 3.04 (m, 1H), 3.08 (s, 3H), 3.11 (s, 3H), 6.92 (d, J=10 Hz, 1H), 7.00 (d, J=10 Hz, 1H), 7.22 (d, J=14.8 Hz, 1H), 7.32 (d, J=14.8 Hz, 1H), 7.69 (d, J=15.6 Hz, 1H), 7.95 (d, J=15.6 Hz, 1H), 8.02 (s, 2H), 8.09 (s, 1H), 8.17 (s, 1H), 9.70 (s, 1H).

Example 2

Bis(trihydroxypropylmethyl)nitrone (B)

Bisaldehyde 20 is synthesized using the procedures shown in Example 1. Bisaldehyde 20 is reacted with 4-(hydroxyamino)-4-(3-hydroxypropyl)heptane-1,7-diol in pyridine to produce nitrone B.

Example 3

P Formation of Oxime C

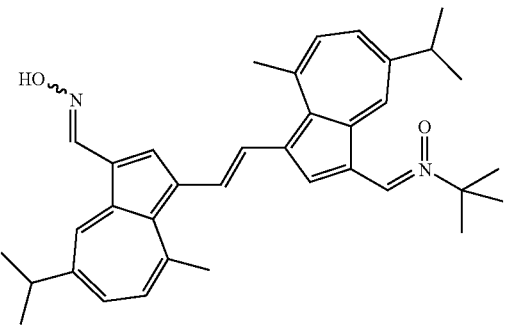

(C)

Mononitrate aldehyde 22

Bisaldehyde 20 was reacted with one equivalent of N-tert-butylhydroxylamine hydrochloride to form mononitrone aldehyde 22.

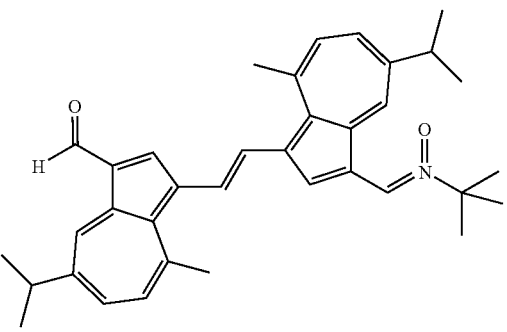

(22)

Oxime C

Aldehyde 22 is then reacted with NH₂OH.HCl in pyridine solvent at elevated temperature to form oxime C.

Example 4

2,2-Dimethylpyrroline N-oxide derivative D

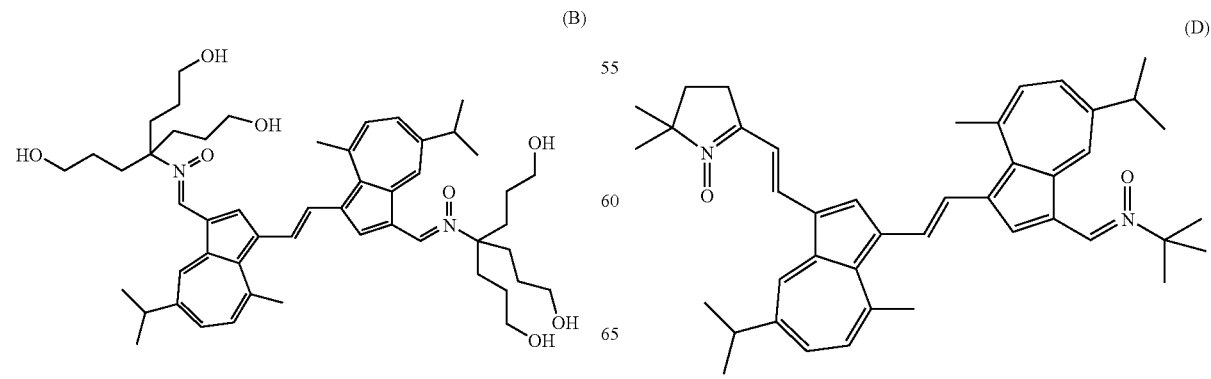

(B)

(D)

Mononitrone aldehyde 22 is prepared in accordance with the procedures illustrated in Examples 1 and 3. Aldehyde 22 is dissolved in THF and reacted with 2-(2-lithiomethyl)-5,5-dimethylpyrroline N-oxide in THF at elevated temperature to form derivative D.

Example 5

Sodium Sulfonate E

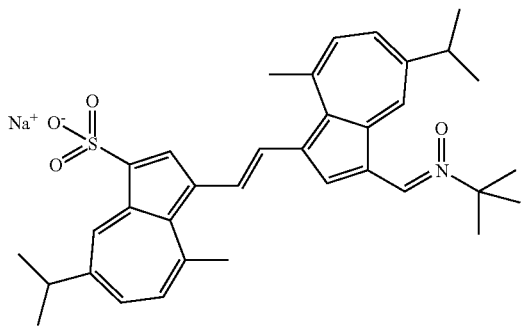

(E)

Mononitrone A is synthesized in accordance with the procedure illustrated in Example 1, dissolved in pyridine and then reacted with $SO_3$ in the presence of a sodium bicarbonate catalyst to produce compound E.

Example 6

Ethyl Ester (F)

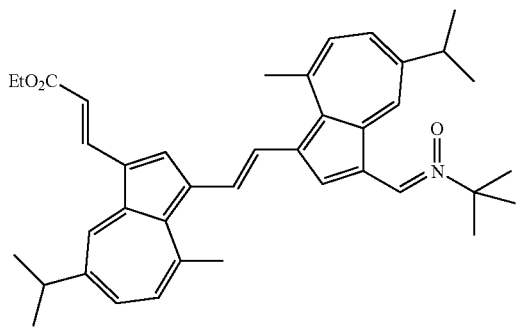

(F)

Mononitrone aldehyde 22, produced in accordance with the procedure illustrated in Example 2, is dissolved in THF and reacted with

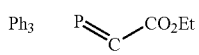

Example 7

Dithiane Nitrone (STNXY) (G)

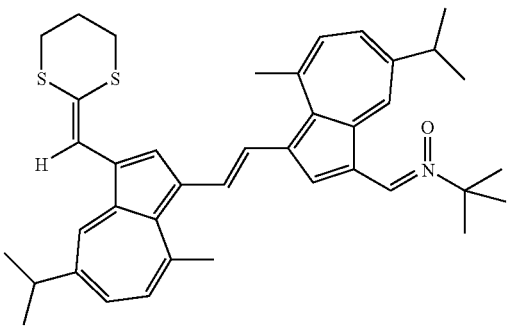

(G)

2-trimethyl silyl-1,3dithiane (80 mg, 0.41 mmol) was dissolved in 0.5 ml THF at −80° C. and 0.23 ml of 2M nBuLi was added with stirring at −80° C. The resulting mixture was added to a solution of mononitrone 22 (195 mg, 0.38 mmol) dissolved in 2 ml THF at −50° C. and allowed to warm slowly to room temperature. The solvent was evaporated under reduced pressure. The residue was dissolved in chloroform and purified by silica gel column chromatography using chloroform as the eluting solvent $R_f$ 0.63 Chloroform, resulting in dithiane nitrone (G). IR (CHCl$_3$) 2962, 1538, 1435; $^1$H NMR (400 MHz, CDCl$_3$) δ 1.36 (d, J=6.9 Hz, 6H), 1.37 (d, J=6.9 Hz, 6H), 1.75 (s, 9H), 3.0-3.08 (multiplet, 8H), 3.11 (s, 3H), 3.15 (s, 3H), 6.95 (d, J=10.7 Hz, 2H), 7.05 (d, J=10.6 Hz, 2H), 7.31 (s, 1H), 7.32 (s, 1H), 7.35 (d, J=10.6, 2H), 7.46 (s, 1H), 7.77 (d, J=15.5 Hz, 1H), 7.92 (d, J=15.5 Hz, 1H), 8.15 (d, J=18, 1H), 8.19 (s, 1H), 9.73 (s, 1H); $^{13}$C NMR (100 MHz, D$_2$O) δ24.7, 24.8, 28.9, 29.2, 29.3, 30.3, 31.1, 38.3, 38.4, 69.9, 118.9, 123.5, 124.0, 124.1, 125.6, 126.3, 126.9, 129.2, 130.3, 131.2, 132.0, 133.9, 134.2, 135.8, 136.1, 136.2, 137.1, 137.6, 140.1, 141.7, 142.4, 143.3, 148.0, 148.3; LRMS (LC/MS APCI MeOH) m/e 622 (MH+).

Example 8

Cyclohexyl Nitrone Derivative (H)

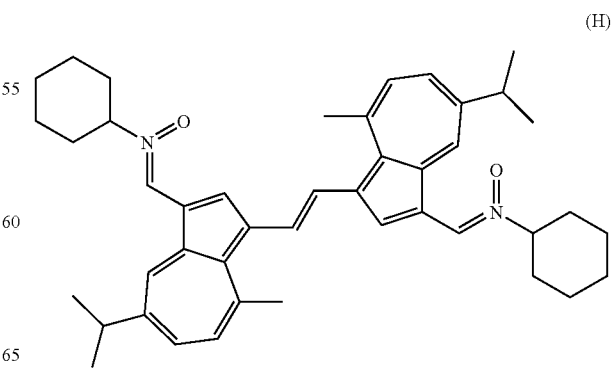

(H)

Dialdehyde 20 is synthesized in accordance with the procedure of Example 1 and then reacted with N-cyclohexylhydroxylamine hydrochloride in pyridine to form derivative (H).

Example 9

Methoxy Enol Ether (I)

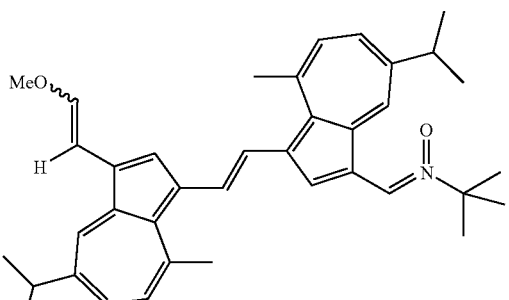
(I)

(Methoxymethyl)triphenylphosphonium chloride (64 mg, 0.19 mmol) was stirred in 1 ml of THF and 0.1 ml of 2M BuLi was added to −25° C. producing a red solution. The red solution was added to a solution of mononitrone 22 (100 mg, 0.17 mmol) in 0.5 ml THF. The mixture was stirred at room temperature for 15 hours. After washing with saturated ammonium chloride and extracting with dichloromethane, a new, less polar compound was visible by TLC in addition to the starting material. The product was purified by silica gel column chromatography using 100:1 $CH_2Cl_2$:EtOAc yielding 42 mg of I as a mixture of cis/trans isomers (39%). Mp 235° C.decomp. $R_f$ 0.63 dichloromethane/ethyl acetate (20:1).IR($CHCl_3$) 2958, 1542, 1436. Because it was not possible to separate the cis and trans isomers, the resulting $^1$H NMR spectrum is not sufficient for definitive characterization. Nevertheless the spectrum has been interpreted as follows: $^1$H NMR (400 MHz, $CDCl_3$) δ 1.36-1.41 (m, 24H), 1.75 (s, 18H), 3.07-3.13 (m, 3H), 3.82 (s, 3H), 3.86 (s, 3H), 5.84 (d, J=6.8 Hz, 1H), 6.30 (d, J=6.8 Hz, 1H), 6.35 (d, J=12 Hz, 1H), 6.90-8.31 (m, H), 8.55 (s, 1H), 9.7 (s, 1H); LRMS (LC/MS APCI MeOH m/e 548 (MH+).

Example 10

2,2-Dimethylpyrroline N-oxide-STAZN derivative (J)

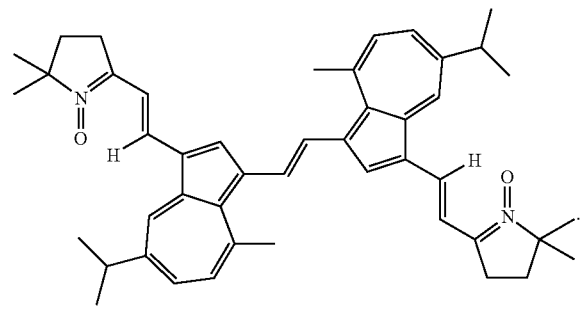
(J)

Lithium diisopropylamide (0.2 ml of 2 M solution was added to 2,5,5-trimethylpyrroline N-oxide cooled to −25° C.

A reddish-orange color was observed. Bisaldehyde 20 (100 mg, 0.22 mmol) in 10 ml THF was added with stirring and warmed to room temperature. The reaction mixture was washed with ammonium chloride and the product isolated by flash chromatography using chloroform with increasing concentrations of 2-propanol. The resulting green product, was stirred in toluene with excess magnesium sulfate for four hours at 100° C. $R_f$ Chloroform. IR ($CHCl_3$) 2959, 1538, 1440, 1370. $^1$H NMR (400 MHz, $CDCl_3$) δ 1.35 (d, J=6.9 Hz, 12H), 1.49 (s, 12H), 2.13 (t, J=7.3 Hz, 4H), 2.98 (t, J=7.3 Hz, 4H), 3.04 (m, 2H), 3.11 (s, 6H), 7.01 (d, J=7.3 Hz, 2H), 7.32 (dd, J=10.8, 7=1.6 Hz, 2H), 7.40 (d, J=18.0 Hz, 2H), 7.525 (d, J=18.0 Hz, 2H), 7.73 (s, 2H), 8.22 (d, J=1.6 Hz, 2H), 8.54 (s, 2H); $^{13}$C NMR (100 MHz, $D_2O$) δ 24.7, 26.0, 29.1, 29.9, 33.0, 38.4, 73.9, 114.0, 125.7, 126.4, 127.8, 130.7, 131.0, 132.9, 133.5, 137.0, 137.1, 139.7, 142.6, 143.3, 148.6; LRMS (LC/MS APCI MeOH m/e 667 (MH+).

Example 11

STAZN Derivative (K)

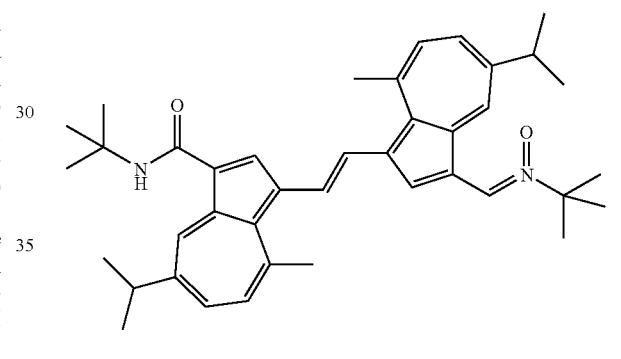
(K)

STAZN (21) was prepared in accordance with procedures illustrated in the Journal of the American Chemical Society: Becker et al., "Stilbazulenyl Nitrone (STAZN): A Nitronyl-Substituted Hydrocarbon with the Potency of Classical Phenolic Chain-Breaking Antioxidants", *J. Am. Chem. Soc.* 2002, 124:4678-84.

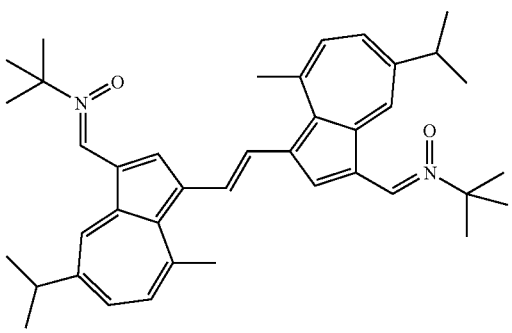
STZN (21)

STAZN (21) is reacted with 4-toluene-sulfonyl chloride in pyrridine to form derivative K.

Example 12

Hydrazone Derivative (L)

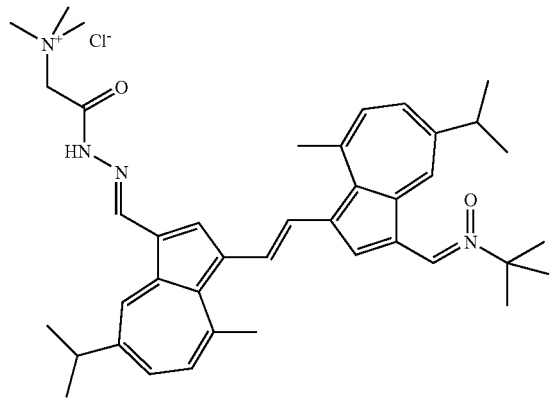

(L)

Mononitrone monoaldehyde (22) is prepared in accordance with the procedures illustrated in Examples 1 and 3, and reacted with trimethylacethydrazide ammonium chloride (Girard's Reagent T) to form derivative (L).

Example 13

STAZN Derivative (M)

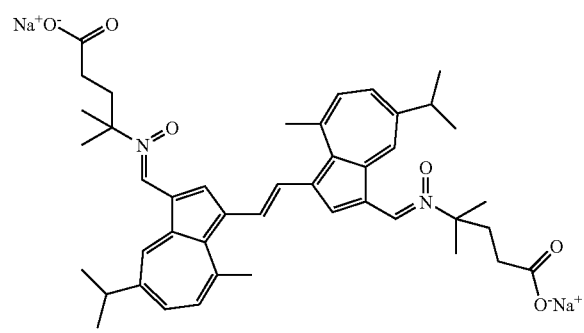

(M)

Dialdehyde 20 is reacted with sodium-4-(hydroxyamino)-4-methylpentanoate in ethanol to form derivative M.

Example 14

STAZN Derivative (N)

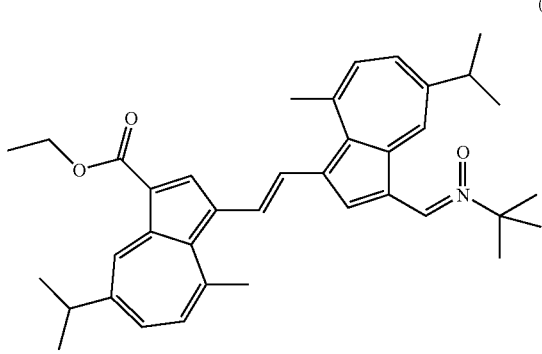

(N)

Mononitrone A is prepared in accordance with the procedure of Example 1 and reacted with oxalyl bromide in a solvent mixture comprising ethanol and diethylether to form derivative N.

Example 15

Methoxy Derivative (O)

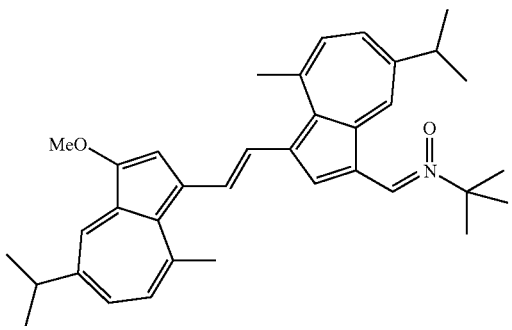

(O)

Mononitrone A is reacted with

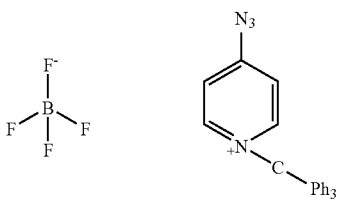

and methanol to form derivative O.

Example 16

Sodium Sulfonate Derivative (P)

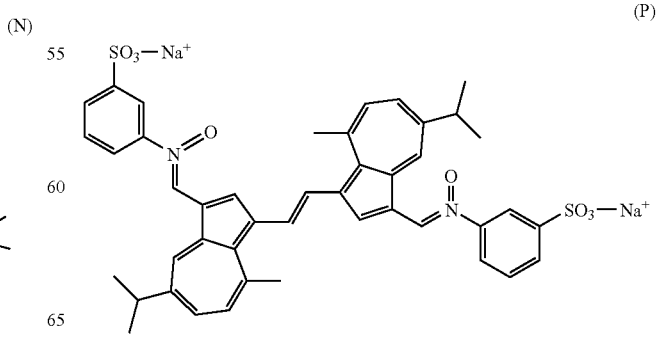

(P)

Dialdehyde 20 is reacted with sodium N-3-sulfonatophenyl hydroxyl-amine in ethanol solvent to form derivative P.

Example 17

Ethyl Mercaptan Derivative (Q)

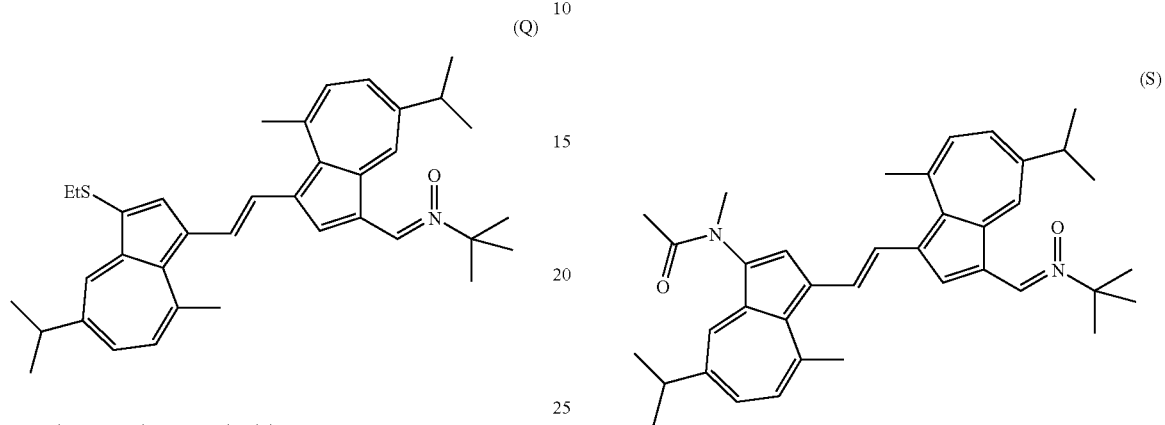

(Q)

Mononitrone A is reacted with

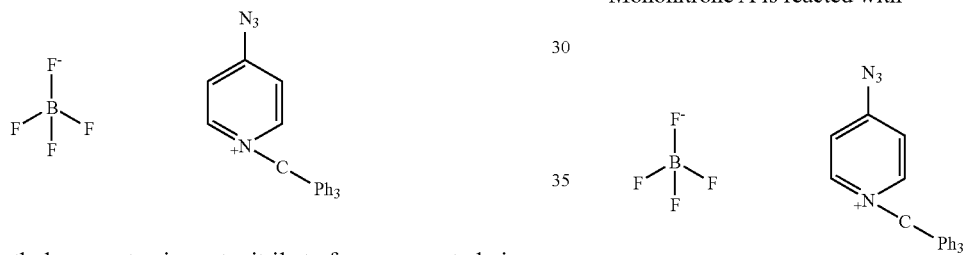

and ethyl mercaptan in acetonitrile to form mercaptoderivative Q.

Example 18

STAZN Derivative (R)

(R)

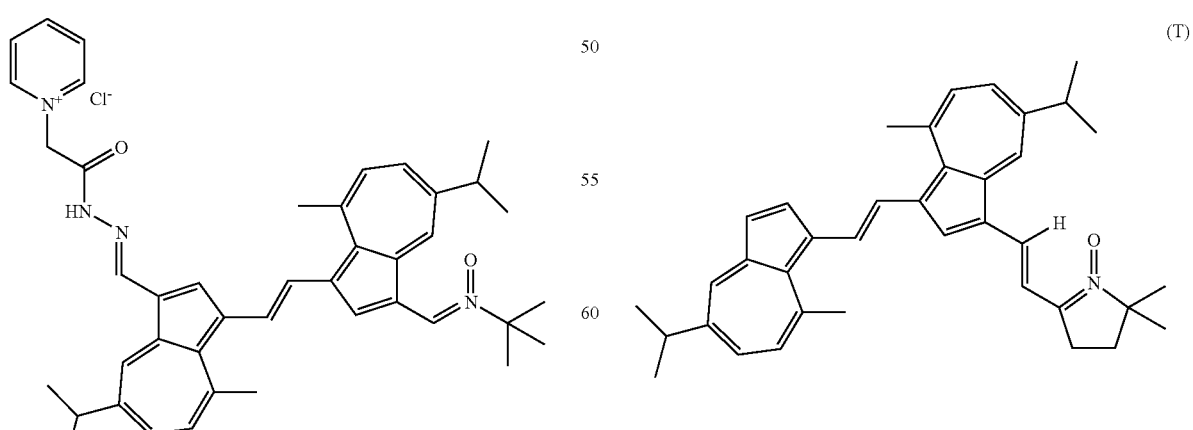

Mononitrone monoaldehyde (22) was reacted with (carboxy methyl)pyridinum chloride hydrazide (Girard's Reagent P) in ethanol solvent to form derivative R.

Example 19

STAZN Derivative (S)

(S)

Mononitrone A is reacted with and N-methylacetamide in acetonitrile to form derivative S.

Example 20

2,2-Dimethylpyrroline N-oxide derivative (T)

(T)

Lithium diisopropylamide (0.2 ml of 2 M solution is added to 2,5,5-trimethylpyrroline N— oxide cooled to −25° C. The monoaldehyde 34 (0.22 mmol) in 10 ml THF is added with stiffing and warmed to room temperature. The reaction mixture washed with ammonium chloride and the product isolated by flash chromatography to yield the title pyrroline N-oxide derivative (T).

Example 21

Antioxidant Assay

STAZN and STNXY (Dithiane Nitrone G)

In the following example, comparative testing of the antioxidant activity of azulenyl nitrone compounds of the invention against a control, was performed. The assay was based on the well-established oxidation of cumene to cumene hydroperoxide by atmospheric oxygen at 37° C. in the presence of the free radical initiator AIBN (Blanchard, H. S. *J. Am. Chem. Soc.* (1959) 81:4548; Characterization of products formed during the autoxidation of beta carotene. Handelman, G. J., van Kujik, F. J. G. M., Chatterjee, A., Krinsky, N. I. *Free Rad. Biol. Med.* (1991) 10: 427-37). The progress of the peroxidation reaction is conveniently followed and quantified by 1H NMR spectroscopy by monitoring the appearance and increasing integration of the singlet arising from the methyl groups of cumene hydroperoxide. The use of a long, low power, selective pulse (Shaped radiofrequency pulses in high resolution NMR. Freeman, R. J. Prog. Nuc. Mag. Spec. (1998) 32:59) allowed the growth of the cumene hydroperoxide methyl group singlet to be accurately measured in the presence of a huge excess of cumene. This was shown by using known concentrations of commercially available cumene hydroperoxide to calibrate the peak areas. The concentration of internal standard (bis-1,4-(trichloromethyl)benzene) was shown to be invariant under the reaction conditions. The results of the assay are presented in FIG. 1.

FIG. 1 reveals that STAZN and the mononitrone STNXY (Dithiane nitrone G) both possess remarkable potency as nitrone-based chain breaking antioxidants. Accordingly, as can be seen from the above data, the azulenyl nitrone compounds of the present invention possess significant or potent free-radical scavenging/antioxidant activity. Indeed, many of the nitrone compounds of the invention display comparable or even greater antioxidant activity than PBN. Accordingly, the azulenyl nitrone compounds of the invention are potential therapeutic agents useful for the treatment and/or prevention of diseases or conditions that have been reported to be amenable to antioxidant therapy or involve free-radical generation. Such diseases or conditions include, but are not limited to, pain conditions, autoimmune diseases or conditions, inflammatory diseases or conditions, and neurological or neurodegenerative diseases or conditions.

Non-limiting examples of pain conditions that arise from or are characterized by oxidative damage or oxidative stress are: migraine (See, e.g., Ciancarelli, I. et al, 2003, Urinary Nitric Oxide Metabolites and Lipid Peroxidation By-Products in Migraine, *Cephalalgia,* 23(1): 39-42); acute, chronic and neuropathic pain syndromes and neuralgias (See, e.g., De las Heras Castano, G. et al., 2000, Use of Antioxidants to Treat Pain in Chronic Pancreatitis, *Rev. Esp. Enferm. Dig.,* 92(6):375-85); irritable bowel syndrome; and nerve injury and neuropathies including diabetic neuropathy (See, e.g., Gray, C. et al., 2003, Neuroprotective Effects of Nitrone Radical Scavenger S-PBN on Reperfusion Nerve Injury in Rats, *Brain Res.,* 982(2):179-85, and Strokov, I. A. et al., 2000, The Function of Endogenous Protective Systems in Patients with Insulin-Dependent Diabetes Mellitus and Polyneuropathy: Effect of Antioxidant Therapy, *Bull. Exp. Biol. Med.,* 130(10):986-90). Non-limiting examples of autoimmune diseases or conditions that arise from or are characterized by oxidative damage or oxidative stress are: multiple sclerosis (See, e.g., Liu, Y. et al., 2003, Bilirubin as a Potent Antioxidant Suppresses Experimental Autoimmune Encephalomyelitis: Implications for the Role of Oxidative Stress in the Development of Multiple Sclerosis, *J. Neuroimmunol,* 139(1-2): 27-35); arthritis; diabetes and related complications (See, e.g., Tabatabaie, T. et al., 1997, Spin Trapping Agent Phenyl-N-tert-butylnitrone Protects against the Onset of Drug-Induced Insulin-Dependent Diabetes Mellitus, *FEBS Lett.,* 407(2):148-52); and Graves' disease and other thyroid disorders (See, e.g., Vrca, V. B. et al., 2004, Supplementation with Antioxidants in the Treatment of Graves' Disease: the Effect on Glutathione Peroxidase Activity and Concentration of Selenium, *Clin. Chim. Acta.,* 341(1-2): 55-63).

Non-limiting examples of inflammatory diseases or conditions that arise from or are characterized by oxidative damage or oxidative stress are: myocardial infarction and dysfunction (See, e.g., Vergely, C. et al., 2003, Effect of Two New PBN-Derived Phosphorylated Nitrones against Postischaemic Ventricular Dysrhythmias, *Fundam. Clin. Pharmacol.,* 17(4):433-42); arteriosclerosis and other vascular diseases (See, e.g., Micheletta, F. et al., 2004, Vitamin E Supplementation in Patients with Carotid Atherosclerosis: Reversal of Altered Oxidative Stress Status in Plasma But Not in Plaque, *Arterioscler. Thromb. Vace. Biol.,* 24(1):136-40); asthma, reactive airway diseases and allergies (See, e.g., Nadeem, A. et al., 2003, Increased Oxidative Stress and Altered Levels of Antioxidants in Asthma, *J. Allergy Clin. Immunol.,* 111(1): 72-8); transplant and graft failure or rejection (See, e.g., Connor, H. D. et al., 1992, Evidence that Free Radicals Are Involved in Graft Failure following Orthotopic Liver Transplantation in the Rat—an Electron Paramagnetic Resonance Spin Trapping Study, *Transplantation,* 54(2):199-204); lung injury and damage (See, e.g., Murphy, P. G. et al., 1991, Direct Detection of Free Radical Generation in an in vivo Model of Acute Lung Injury, *Radical Res. Commun.,* 15(3): 167-76); hepatitis and jaundice-induced liver disorders (See, e.g., Yamashita, T. et al., 1996, The Effects of α-Phenyl-tert-butylnitrone (PBN) on Copper-Induced Rat Fulminant Hepatitis with Jaundice, *Free Radical Biol. Med.,* 21(6):755-61); pancreatitis and other pancreatic disorders (See, e.g., Koiwai, T. et al., 1989, The Role of Oxygen Free Radicals in Experimental Acute Pancreatitis in the Rat, *Int. J. Pancreatol,* 5(2): 135-43); inflammatory bowel disease including Crohn's disease and other disorders of the digestive tract (See, e.g., Reimund, J. M. et al., 1998, Antioxidants Inhibit the in vitro Production of Inflammatory Cytokines in Crohn's Disease and Ulcerative Colitis, *Eur. J. Clin. Invest.,* 28(2): 145-50); retinal ischemia and damage including macular degeneration and other degenerative or inflammatory disorders of the retina and eye (See, e.g., F. Block and M. Schwarz, 1997, Effects of Antioxidants on Ischemic Retinal Dysfunction, *Exp. Eye Res.,* 64(4): 559-64); renal ischemia and kidney disorders (See, e.g., Kadkhodaee, M. et al., 1996, Detection of Hydroxyl and Carbon-Centered Radicals by EPR Spectroscopy after Ischaemia and Reperfusion of the Rat Kidney, *Free Radical Res.,* 25(1):31-42); and endotoxemia (See, e.g., Harkins, J. D. et al., 1997, Effect of α-Phenyl-tert-butylnitrone on Endotoxin Toxemia in Horses, *Vet. Hum. Toxicol.,* 39(5):268-71).

Non-limiting examples of neurological or neurodegenerative diseases or conditions that arise from or are characterized by oxidative damage or oxidative stress are: stroke (See, e.g., Marshall, J. W. et al, 2001, NXY-059, a Free Radical-Trapping Agent, Substantially Lessens the Functional Disability Resulting from Cerebral Ischemia in a Primate Species, *Stroke,* 32(1):190-98, and Ginsberg, M. D. et al, 2003, Stilbazulenyl Nitrone, a Novel Antioxidant, Is Highly Neuroprotective in Focal Ischemia, *Ann. Neurol,* 54(3):330-42); schizophrenia and other disorders of cognition (See, e.g., Dakhale, G. et al, 2004, Oxidative Damage and Schizophrenia: the Potential Benefit by Atypical Antipsychotics, *Neuropsychobiol,* 49(4):205-09); mood disorders and other disorders of affect (See, e.g., Ranjekar, P. K. et al., 2003, Decreased Antioxidant Enzymes and Membrane Essential Polyunsaturated Fatty Acids in Schizophrenic and Bipolar Mood Disorder Patients, *Psychiatry Res.,* 121(2):109-22); epilepsy (See, e.g., Gupta, M. et al, 2004, Add-on Melatonin Improves Quality of Life in Epileptic Children on Valproate Monotherapy: a Randomized, Double-Blind, Placebo-Controlled Trial, *Epilepsy Behav.,* 5(3):316-21); aging and senescence (See, e.g., Carney, J. M. et al, 1991, Reversal of Age-Related Increase in Brain Protein Oxidation, Decrease in Enzyme Activity, and Loss in Temporal and Spatial Memory by Chronic Administration of the Spin-Trapping Compound N-tert-Butyl-α-phenylnitrone, *Proc. Natl. Acad. Sci. USA,* 88(9):3633-6); Parkinson's disease (See, e.g., Fredriksson, A. et al, 1997, MPTP-Induced Deficits in Motor Activity: Neuroprotective Effects of the Spin-Trapping Agent, α-Phenyl-tert-butylnitrone (PBN), J. Neural. Transm., 104(6-7): 579-92); Alzheimer's disease (See, e.g., Butterfield, D. A. et al, 1996, A (25-35) Peptide Displays $H_2O_2$-Like Reactivity towards Aqueous $Fe^{2+}$, Nitroxide Spin Probes, and Synaptosomal Membrane Proteins, *Life Sci,* 58(3):217-28); Huntington's disease (See, e.g., Nakao, N. et al., 1996, Antioxidant Treatment Protects Striatal Neurons against Excitotoxic Insults, *Neuroscience,* 73(1):185-200); amyotrophic lateral sclerosis (See, e.g., Desnuelle, C. et al, 2001, A Double-Blind, Placebo-Controlled Randomized Clinical Trial of α-Tocopherol (Vitamin E) in the Treatment of Amyotrophic Lateral Sclerosis, *Amyotrophic Lateral Scler. Other Motor Neuron Disorders,* 2(1):9-18); and head, trauma and traumatic brain injury (See, e.g., Sen, S. et al, 1994, α-Phenyl-tert-butylnitrone Inhibits Free Radical Release in Brain Concussion, *Free Radical Biol. Med.,* 16(6):685-91, and Marklund, N. et al, 2001, Effects of the Nitrone Radical Scavengers PBN and S-PBN on in vivo Trapping of Reactive Oxygen Species after Traumatic Brain Injury in Rats, *J. Cereb. Blood Flow Metab.,* 21(11); 1259-67).

All publications, patents and patent applications cited in this specification are herein incorporated by reference as if each individual publication or patent application were specifically and individually indicated to be incorporated by reference. Although the foregoing invention has been described in some detail by way of illustration and example for purposes of clarity of understanding, it will be readily apparent to those of ordinary skill in the art in light of the teachings of this invention that certain changes and modifications may be made thereto without departing from the spirit or scope of the appended claims. All such changes and modifications included herein.

What is claimed is:
1. A compound having the formula:

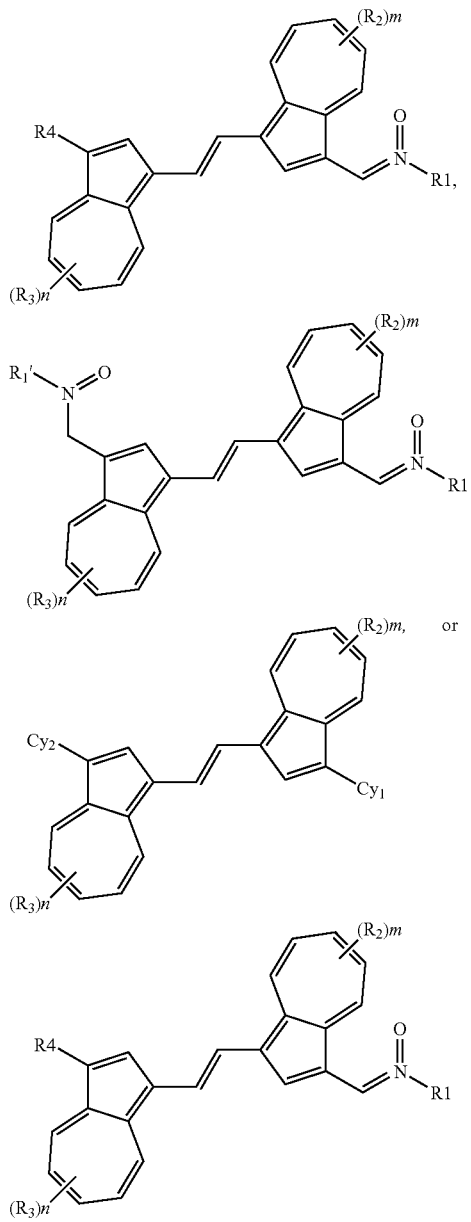

wherein
m and n is independently 0, 1, 2 or 3;
$R^1$ is independently selected from the group consisting of substituted or unsubstituted alkyl, cycloalkyl, heterocycloalkyl and aryl;
each of $R^2$ and $R^3$ is independently alkyl;
$R^4$ is H, substituted or unsubstituted alkyl, CHO, hydroxyl, substituted or unsubstituted alkoxy, substituted or unsubstituted alkoxycarbonyl, substituted or unsubstituted alkylthio, substituted or unsubstituted acylamino, substituted or unsubstituted. amido, $SO_3H$, C(H)=NOH, $Cy^2$,

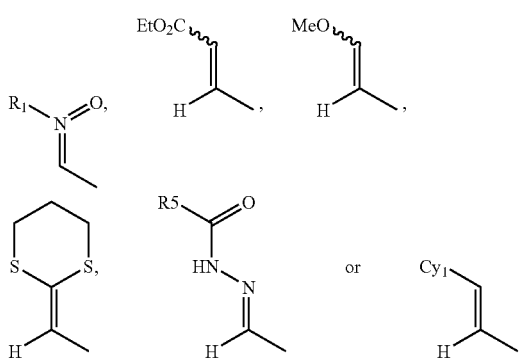
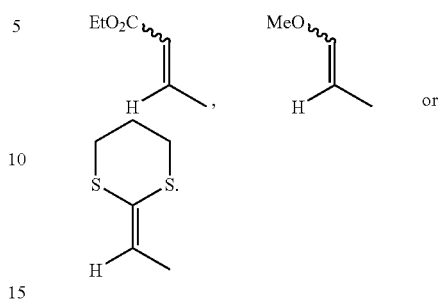

R[5] is amino, aminomethyl, dialkylaminomethyl, or trialkylaminomethyl quarternary salt;
each of Cy[1] and Cy[2] is independently

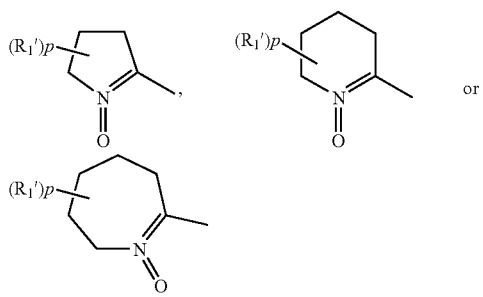

R[1'] is alkyl; p is 0, 1, or 2;
and
provided when R[4] is CHO, R[1] is selected from the group consisting of substituted alkyl, substituted aryl, substituted or unsubstituted cycloalkyl, and substituted or unsubstituted heterocycloalkyl;
or a pharmaceutically acceptable salt or solvate thereof;
and stereoisomers and tautomers thereof.

2. A compound of claim 1 wherein m is 1 or 2.
3. A compound of claim 1 wherein n is 1 or 2.
4. A compound of claim 1 wherein each of m and n is 2.
5. A compound of claim 1 wherein each of m and n is 2 and each of R[2] and R[3] is alkyl.
6. A compound of claim 5 wherein one R[2] is methyl and the other R[2] is isopropyl.
7. A compound of claim 5 wherein one R[3] is methyl and the other R[3] is isopropyl.
8. A compound of claim 1 wherein R[1] is substituted or unsubstituted alkyl or substituted or unsubstituted aryl.
9. A compound of claim 1 wherein R[1] is substituted or unsubstituted cycloalkyll or substituted or unsubstituted heterocycloalkyl.
10. A compound of claim 1 wherein R[1] is t-butyl or substituted t-butyl.
11. A compound of claim 1 wherein R[1] is —C(CH$_2$CH$_2$CH$_2$OH)$_3$, 3-(SO$_3$H)Ph, or —C(Me)$_2$CH$_2$CH$_2$CO$_2$H.
12. A compound of claim 1 wherein R[1] is cycloalkyll.
13. A compound of claim 1 wherein R[1] is cyclohexyl.
14. A compound of claim 1 wherein R[1] is phenyl, substituted phenyl, or benzyl.

15. A compound of claim 1 wherein R[4] is H, alkyl, hydroxy, alkoxy, alkoxycarbonyl, alkylthio, amido, C(H)=NOH,

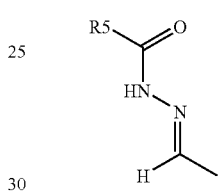

16. A compound of claim 1 wherein R[4] is H, OMe, SMe, SEt, SO$_3$H, —NHAc, —N(Me)Ac, —CONH-t-Bu, or OEt.
17. A compound of claim 1 wherein R[4] is substituted amido, acyl amino, or Cy[2].
18. A compound of claim 1 wherein R[4] is

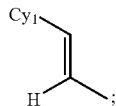

and wherein R[5] is amino, aminomethyl, dialkylaminomethyl, trialkylaminomethyl quarternary salt, —CH$_2$NMe$_2$,

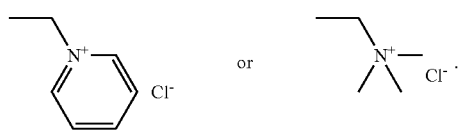

19. A compound of claim 1 wherein R[4] is

Cy[1] is

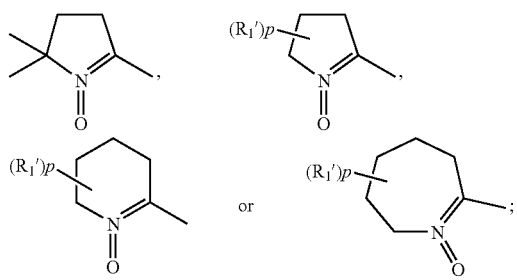

and R[1'] is alkyl; and p is 0, 1, or 2.

20. A compound of claim 1 wherein the compound is selected from the group consisting of

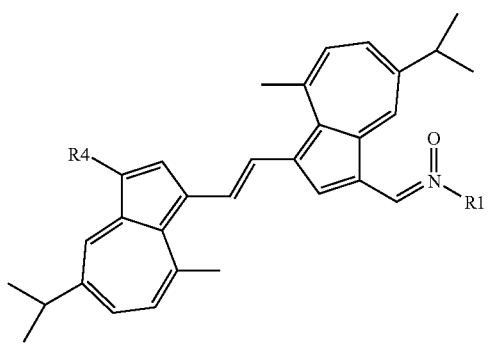

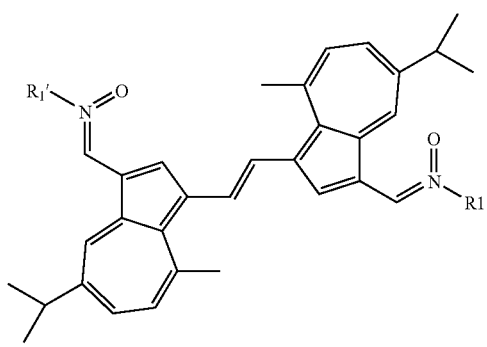

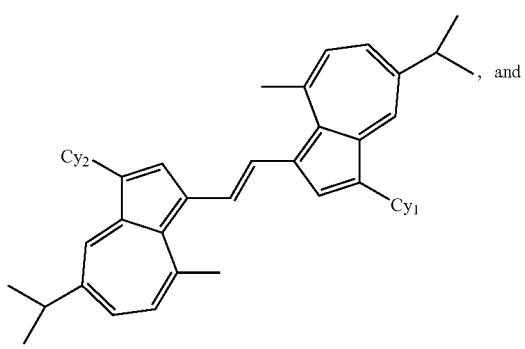, and

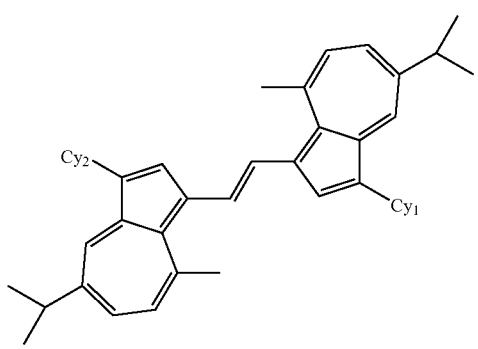

21. A compound having a structure

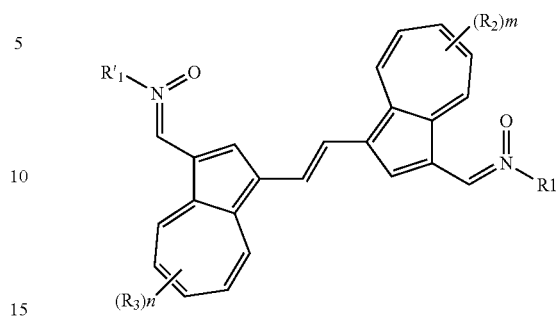

wherein $R^1$ is selected from substituted alkyl, substituted aryl, substituted or unsubstituted cycloalkyl, and substituted or unsubstituted heterocycloalkyl;

$R^{1'}$ is selected from substituted or unsubstituted alkyl, cycloalkyl, herterocycloalkyl, and aryl;

each of $R^2$ and $R^3$ is independently alkyl;

or a pharmaceutically acceptable salt or solvate thereof.

22. The compound of claim 21 having a structure

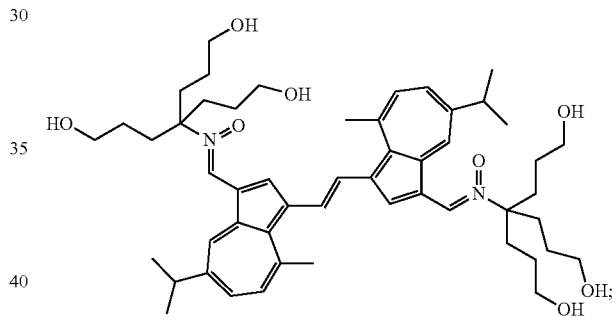

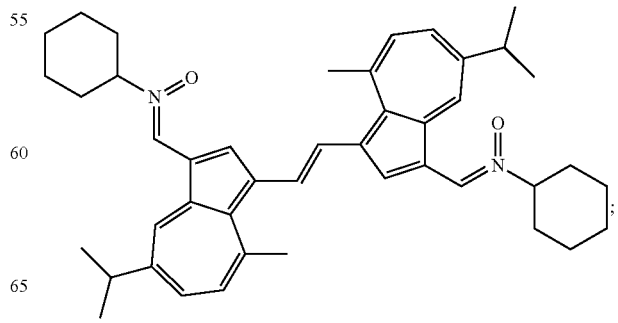

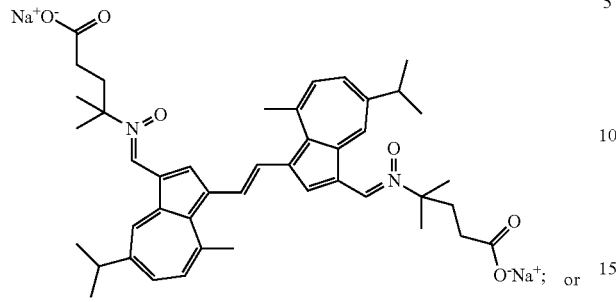
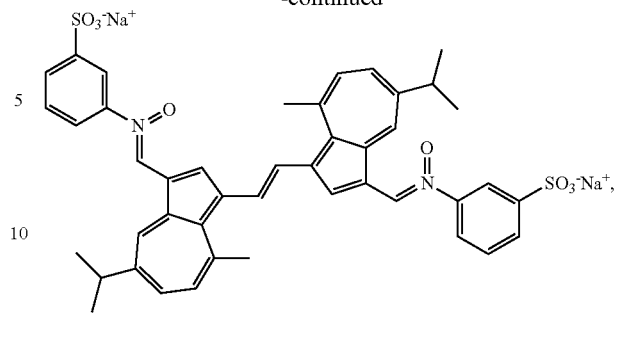
or a pharmaceutically acceptable salt or solvate thereof.
* * * * *

UNITED STATES PATENT AND TRADEMARK OFFICE
CERTIFICATE OF CORRECTION

| | |
|---|---|
| PATENT NO. | : 7,910,729 B2 |
| APPLICATION NO. | : 11/662352 |
| DATED | : March 22, 2011 |
| INVENTOR(S) | : David A. Becker et al. |

It is certified that error appears in the above-identified patent and that said Letters Patent is hereby corrected as shown below:

At Column 58, line 7, delete the first two formulas.

At Column 58, line 66, "unsubstituted." should be -- unsubstituted --.

At Column 61, line 25, delete $2^{nd}$ and $3^{rd}$ formulas.

Signed and Sealed this
Sixth Day of December, 2011

David J. Kappos
*Director of the United States Patent and Trademark Office*